(12) United States Patent
Happe

(10) Patent No.: US 6,858,718 B1
(45) Date of Patent: Feb. 22, 2005

(54) HYDROGEN PRODUCTION

(75) Inventor: Thomas Happe, Euskirchen (DE)

(73) Assignee: Melis Energy, Santa Barbara, CA (US)

( * ) Notice: Subject to any disclaimer, the term of this patent is extended or adjusted under 35 U.S.C. 154(b) by 0 days.

(21) Appl. No.: 10/077,699

(22) Filed: Feb. 15, 2002

Related U.S. Application Data

(60) Provisional application No. 60/269,872, filed on Feb. 16, 2001.

(51) Int. Cl.$^7$ .......................... C07H 21/04; C12N 9/04; C12N 15/00; C12N 1/20
(52) U.S. Cl. .................. 536/23.2; 435/190; 435/252.3; 435/320.1
(58) Field of Search ............................. 435/190, 252.3, 435/320.1, 189; 536/23.2

(56) References Cited

PUBLICATIONS

Mets. GenBank Database—Acession # AF289201, Aug., 2000.*

* cited by examiner

Primary Examiner—P. Achutamurthy
Assistant Examiner—Yong D. Pak
(74) Attorney, Agent, or Firm—Michael G. Petit

(57) ABSTRACT

The enzyme, iron hydrogenase (HydA), has industrial applications for the production of hydrogen, specifically, for catalyzing the reversible reduction of protons to molecular hydrogen. The present invention relates to the isolation of a nucleic acid sequence from the algae *Scenedesmus obliquus*, *Chlamydomonas reinhardtii*, and *Chlorella fusca* that encodes iron hydrogenase. The invention further discloses the genomic nucleic acid, c-DNA and the protein sequences for HydA. The genes and gene products may be used in a photosynthetic process for hydrogen production which includes growing a microorganism containing the gene coding for HydA in a culture medium under illuminated conditions sufficient to accumulate an endogenous substrate; depleting a nutrient selected from the group consisting of sulfur, iron, and manganese from the medium; then allowing the culture to become anaerobic by consumption of an endogenous or exogenous substrate in the light.

3 Claims, 5 Drawing Sheets

Figure 6

HYDROGEN PRODUCTION

CROSS REFERENCE TO RELATED APPLICATIONS

This application claims the benefit of U.S. Provisional Application Ser. No. 60/269,872, which was filed with the U.S. Patent and Trademark Office on Feb. 16, 2001.

BACKGROUND OF THE INVENTION

1. Field of the Invention

The present invention relates to the isolation of a nucleic acid sequences that encode an enzyme that catalyzes the transfer of electrons to protons for the production of molecular hydrogen, and more particularly to iron hydrogenase and genes encoding for the iron hydrogenase in microscopic organisms known as unicellular green algae.

2. Prior Art

Molecular hydrogen is currently being considered as a candidate for replacing or supplementing fossil fuels and as a source of clean energy. A potential method for producing hydrogen on a commercial scale is the photobiological production of hydrogen by eukaryotic organisms. Green algae respond to anaerobic stress by switching the oxidative pathway to a fermentative metabolism. The fermentation of organic compounds and residual photosynthetic electron trasport in the green algae are associated with hydrogen evolution. The key enzyme hydrogenase, which is synthesized only after an anaerobic adaptation, catalyzes the reversible reduction of protons to molecular hydrogen. This method is capable of generating renewable hydrogen fuel from light and water, which are among nature's most plentiful resources.

The ability of green algae, such as *Chlamydomonas reinhardtii*, to produce hydrogen from water has been recognized for over 55 years. This reaction is catalyzed by a reversible hydrogenase, an enzyme that is induced in the cells after exposure to a short period of anaerobiosis. However, the activity of the hydrogenase is rapidly lost when cells are illuminated because of the immediate inactivation of the reversible hydrogenase by photosynthetically generated $O_2$.

Methods have been devised to circumvent the hydrogenase inactivation problem. U.S. Pat. No. 4,532,210 discloses the biological production of hydrogen in an algal culture using an alternating light and dark cycle. The process comprises alternating a step for cultivating the alga in water under aerobic conditions in the presence of light to accumulate photosynthetic products (starch) in the alga, and a step for cultivating the alga in water under microaerobic conditions in the dark to decompose the accumulated material by photosynthesis to evolve hydrogen. This method uses a nitrogen gas purge technique to remove oxygen from the culture.

U.S. Pat. No. 4,442,211 discloses that the efficiency of a process for producing hydrogen, by subjecting algae in an aqueous phase to light irradiation, is increased by culturing algae which has been bleached during a first period of irradiation in a culture medium in an aerobic atmosphere until it has regained color and then subjecting this algae to a second period of irradiation wherein hydrogen is produced at an enhanced rate. A reaction cell is used wherein light irradiates the culture in an environment which is substantially free of $CO_2$ and atmospheric $O_2$. This environment is maintained by passing an inert gas (e.g. helium) through the cell to remove all hydrogen and oxygen generated by the splitting of water molecules in the aqueous medium. Although continuous purging of $H_2$-producing cultures with inert gases has allowed for the sustained production of $H_2$, such purging is expensive and impractical for large-scale mass cultures of algae. In view of the foregoing, there remains a need for a microorganism that produces a hydrogenase enzyme suitable for use in a sustainable process of photosynthetic hydrogen production.

SUMMARY

Accordingly, it is an object of the present invention to provide a gene encoding for hydrogenase and a method for using the gene product for the microbial production of molecular hydrogen. Specifically, the invention provides isolated nucleic acid sequences encoding a stable hydrogenase enzyme (HydA) that will catalyze the reduction of protons to form molecular hydrogen.

Another object of the present invention is to provide isolated nucleic acid sequences encoding a protein that catalyzes the reduction of protons to form molecular hydrogen comprising SEQ. ID. NO. 1. SEQ. ID. NO. 1 comprises a nucleic acid sequence that encodes *Scenedesmus obliquus* HydA.

It is yet a further object of the present invention to provide isolated nucleic acid sequences encoding a protein that catalyzes the reduction of protons to form molecular hydrogen comprising SEQ. ID. NO. 2. SEQ. ID. NO. 2 comprises a nucleic acid sequence that encodes *Chlamydomonas reinhardtii* HydA.

A further object of the present invention is to provide fragments of the nucleic acid sequence comprising SEQ. ID. NO.1 or SEQ. ID. NO.2, encoding iron hydrogenase, that code for products that maintain the biological activity necessary to catalyze the transfer of electrons to protons in a process for producing molecular hydrogen. Such fragments can be either recombinant or synthetic or a combination thereof.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE DRAWINGS

In FIG. 3 (B), the mosaic structure of hydA is illustrated by gray (exons) and white (introns) boxes. The RNA and DNA probes that were used for the blotting experiments are noted on the Figure.

FIG. 6 shown the nucleotide sequence of the hydA cDNA and the deduced amino acid sequence of the hydrogenase from C. reinhardtii.

DESCRIPTION OF THE PREFERRED EMBODIMENTS

Figures 1, 2:
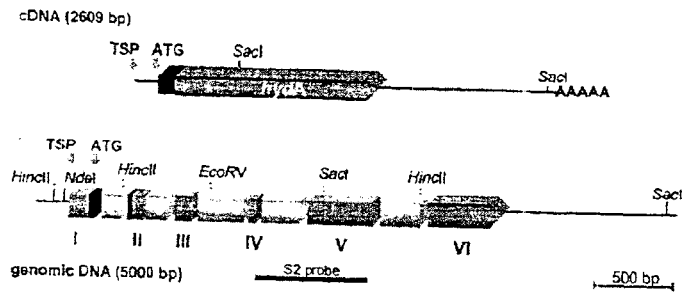
FIG. 1 is a schematic representation of *S. obliquus* HydA genomic and cDNA structures.
FIG. 2 is a comparison of the *S. obliquus-derived* iron hydrogenase amino acid sequence with HydA sequences derived from other organisms.

The isolation, purification and biochemical and genetic characterization of a novel iron hydrogenase from S. obliquus and C. reinhardtii and C. fuscus is disclosed.

I. Scenedesmus obliquus

S. obliquus Algal Strains and Growth Conditions

Wild-type S. obliquus Kützing 276-6 was obtained originally from the culture collection of algae at the University of Göttingen Cells were cultured photoheterotrophically in batch cultures at 25° C. under continuous irradiance of 150 μmol photons per square meter per second. For anaerobic adaptation, 4-liter cultures were bubbled with air supplemented with 5% $CO_2$. After harvesting the cells in the mid-exponential exponential stage of growth, the pellet was resuspended in fresh Tris acetate phosphate (TAP) medium. The algae were anaerobically adapted by flushing the culture with argon in the dark.

Hydrogen Evolution Assay

The in vitro hydrogenase activity was measured by using a Hewlett Packard (HP 5890, Series II) gas chromatograph, equipped with a thermal conductivity detector and a molecular sieve column. Methyl viologen reduced by sodium dithionite was used as an electron donor. 1 unit is defined as the amount of hydrogenase evolving 1 mmol of molecular hydrogen ($H_2$) per minute at 25° C.

The in vivo activity in the presence of different inhibitors of the photosynthetic electron flow was determined as described by Happe et al., in: European Journal of Biochemistry, 214, 475–481 (1993). After anaerobic adaptation, algal cells were harvested, diluted in fresh Tris acetate phosphate medium, and transferred to sealed tubes. Inhibitors were added 1 hour before $H_2$ evolving activity was measured. Cells were broken by sonification. Thylakoid membranes and photosynthetic transport chain remained intact as demonstrated by oxygen polarography. Ferrodoxin of both C. reinhardtii and S. obliquus was isolated according to the method of Schmitter et al. (Eur. J.l of Biochem., 172, pages 405–412 (1988)).

Rapid Amplification of cDNA Ends-Polymerase Chain Reaction (RACE-PCR)

RACE-PCR was performed with the Clontech SMART™RACE cDNA Amplification Kit (Clontech Laboratories, Palo Alto, Calif.) according to the manufacturer's recommendations, except for modification of the PCR and hybridization conditions. Starting material consisted of 1 μg of mRNA from anaerobically adapted cells. The reverse transcription reaction was carried out with a Moloney murine leukemia virus reverse transcriptase in two separate reaction tubes containing either the 5' or the 3' RACE-PCR specific primer from the kit. The cDNA of each sample served as template for the following PCR. For the 5'-RACE-PCR, a Universal Primer Mix (UPM) and the antisense primer, Sc7, were used. The amplification of the 3'-cDNA end was performed with a UPM and the sense primer Sc6. To obtain more distinct PCR signals, the PCR was repeated for both reactions with nested universal primers and designed primers (inverse Sc6 and inverse Sc7, respectively) using a dilution of the products of the first PCR as template.

Primer Extension

RACE-PCR was also implemented to map the transcription initiation site of the hydA mRNA. A gene-specific primer (Sc17) was used to carry out the first strand cDNA synthesis with the Superscript II reverse transcriptase (Life Technologies, Rockville, Md., USA) and 200 ng of mRNA as template. PCR was performed using either Sc12 or Sc27 and the SMART™ specific adapter primer UPM. Two different DNA fragments of 234 bp and 183 bp were amplified under standard PCR conditions. Both fragments were cloned into the pGEM™T-Easy vector (Promega, Madison, Wis., USA) and sequenced using primers from the polylinker of the vector.

Genome Walking with Genomic DNA

Applying the Clontech Walker Kit (Clontech Laboratories), genomic libraries from S. obliquus were generated by digestion with different blunt-end cutting endonucleases (NaeI DraI, PvuIIm, HincII and EcORV) and by adapter ligation at the ends of the resulting DNA fragments. These libraries were utilized as independent templates in five different PCR reactions. Two gene-specific primers (Sc27, Sc35) derived from the hydA cDNA sequence of S. Obliquus were used in combination with a kit adapter primer (AP1) in a first PCR reaction. Subsequently, 1 μl of the first PCR served as a template in a secondary PCR, applying two nested gene-specific primers (i-Sc10, Sc32) along with a nested kit adapter primer (AP2). The resulting products were cloned into pGEM™T-Easy and sequenced. Sequencing was performed by the dideoxy termination method (see, for example: Sanger et al., Proc. Natl. Acad. Sci., U.S,A., 74, 5463–5467 (1977)).

Purification of the Fe-Hydrogenase 40-liter cultures of Scenedesmus obliquus were grown heterotrophically. After centrifugation (10 min, 5000×g) the pellet we re-suspended in 200 ml TAP medium. The cells were anaerobically adapted by flushing the solution with argon for 1 hour in the dark. All further purification steps were performed in an anaerobic chamber (Coylab, Ann Arbor, Mich., USA). The cells were disrupted in a 50 mM Tris/HCl, buffer pH 8.0, 10 mM sodium dithionite by vortexing 3 min with glass beads. The further purification steps were made as described hereinbelow for the isolation of the Fe-hydrogenase of Chlamydomonas reinhardti. Automated Edman degradation of the N-terminal site of the protein was performed with an Applied Biosystem model 477A sequencer with online analysator model 120 A.

RNA Blot Hybridization

Total RNA of S. Obliquus was isolated according to the method described by Johanningmeier et al. (J. Biol. Chem. 259, 13541–13549 (1984)). Equal amounts (20 μg) were separated electrophoretically on 1.2% agarose gels containing formaldehyde. The RNA was transferred onto nylon membranes (Hybond+, Amersham) and hybridized with RNA probes labeled DIG-dUPT using in vitro transcription methodology. A 1.3 kb EcOR1 cDNA fragment was used to detect transcripts with a hydA gene, while a DIG-dUPT-labeled cDNA encoding constitutively expressed plastocyanin, was used as a control. Hybridization reactions were carried out using protocols supplied by the manufacturer (Roche Diagnostics, Mannheim, Germany).

Sequence Analysis Software

Nucleic acid and protein sequences were analyzed with the programs Sci Ed Central (Scientific Educational Software) and ClustalW. The Blast server of the National Center for Biotechnology Information (Bethesda, Md.) was used for database searches.

Recombinant Expression in E. coli

The hydA open reading frame was amplified by PCR using the primer pair Sc29 and Ac30 containing flanking NdeI-BamHI sites. The PCR product was cloned into the pGEM™T-Easy vector. After digestion with NdeI-BamHI, the hydA gene was cloned into the corresponding site of the pET9a expression vector (Promega), producing pLF29.2. The insert of pLF29.2 was sequenced confirming that the fragment contained the exact full coding region of the hydrogenase without transit peptide. E. coli strain BL21 (DE3)pLysS was transformed with pLF29.2. Expression was induced with 1 mM isopropyl-thio-β-D-galactoside at an $OD_{600}$ of 0.3. Pelleted cells were re-suspended in lysis buffer (100 mM Tris/HCl; 4 mM EDTA; 16% Glycine; 2% SDS; 2% Mercaptoethanol; 0.05% Bromophenolblue; 8 M Urea). After heating, the protein extract was separated by 10% SDS-PAGE and blotted onto a PVDF membrane. Western blot analyses were performed using antisera against the Fe-hydrogenase of Chlamydomonas reinhardtii at 1:1000 dilution.

Results for Scenedesmus obliquus

Induction of Hydrogenase Activity and Purification of the Fe-hydrogenase Protein Anaerobic adaptation is the most efficient way to induce hydrogenase activity in Scenedesmus obliquus. Bubbling the alga culture in the dark with argon led to a dramatic increase (10-fold) of hydrogenase activity during the first 2 hours. The enzyme of S. obliquus was purified to homogeneity by successive column chromatography. Since the enzyme is irreversibly inactivated by very low levels of oxygen, all purification steps were performed under strictly anaerobic conditions and in the presence of reducing agents (dithionite). The purification scheme resulted in a 5200-fold purification of HydA with 5% recovery (data not shown). The most powerful step for purifying the protein was a Q-Sepharose high performance column chromatography with pH gradient elution. Gel infiltration chromatography of hydrogenase on a calibrated Superdex-75 column resulted in a single activity peak corresponding to a molecular mass of 45 kDa. The monomeric structure of the enzyme could also be shown on a SDS polyacrylamide gel after Coomassie-blue staining (data not shown). The N-terminal sequence of HydA was determined by Edman degradation. The protein sequence (AGPTAECDRPPAPAPKAXHWQ) is, except for two amino acids, identical to the amino acid sequence deduced from the DNA data (AGPTAECDCPPAPAPKAPHWQ). In the course of the purification procedure there was no indication of a second hydrogenase in S. obliquus because the hydrogenase activity was never separated into distinct fractions. Biochemical data show a high similarity of HydA to the Fe-hydrogenase from C. reinhardtii (Table 1). The enzymes have a high temperature optimum of about 60° C., are strongly inhibited by $O_2$ and CO, and catalyze the $H_2$-evolution with a typical high specific activity. Experiments with inhibitors of translators on ribosomes (data not shown) and analysis of the gene structure show that HydA from S. obliquus is translated in the cytoplasm and transported to the chloroplast.

TABLE I

Biochemical data comparison of purified iron hydrogenases from C. reinhardtii and S. obliquus

|  | C. Reinhardtii | S. obliquus |
| --- | --- | --- |
| Size | 49 kDa | 44.5 kDa |
| Specific activity | 935 U/mg protein | 700 U/mg protein |
| Temperature optimum | 60° C. | 60° C. |
| pH optimum | 6.9 | 7.3 |
| Localization | chloroplast stroma | chloroplast |
| Coding site | nuclear | nuclear |
| pI value | 5.3 | 5.17 |
| $K_M$ value (MV) | 830 μM | 800 μM |
| $K_M$ value (ferredoxin) | 35 μM | Not determined |

Ferredoxin is the Natural Electron Donor of the Fe-Hydrogenase

Hydrogenase activity was determined in intact and broken cells after anaerobic adaptation. The integrity of the photosynthetic electron transport in the sonified cell preparation was demonstrated by the rate of oxygen evolution (154 μmole $O_2$/mg Chl×h). This rate corresponds to 85% of the oxygen evolution measure with intact Scenedesmus cells.

In S. obliquus, the hydrogen evolution is linked to the photosynthetic electron transport chain through PSI. As shown in Table II, the cells were still able to photoproduce hydrogen when electron flow on the PSII was blocked by DCMU. In contrast, addition of DCMIB resulted in inhibition of the $H_2$-production, thus giving evidence of the involvement of PSI in the supply of electrons to hydrogenase. With reference to Table II, after anaerobic adaptation, cells were harvested, diluted in fresh, TAP medium, and incubated with inhibitors as described herein. α-PetF-antibody was raised against spinach ferredoxin. In Table II, DCMU=3-(3,4-dichlorophenyl)-1,1-dimethylurea; DBMIB=2,5-dibromo-3-methyl-6 isopropyl-p-benzochinone; Sulfo-DSPD = sulfodisalicylidinepropanediamin; DCPIP=2,6-dichlorophenolindophenol. The electron transport from PSI to ferredoxin was inhibited using the artificial electron acceptor DCPIP. In this reaction, DCPIP is reduced instead of ferredoxin and electron transfer to hydrogenase is interrupted.

TABLE II

Effects of different photosynthetic inhibitors on hydrogenase activity

|  | Hydrogenase activity Units/mg chlorophyll |
| --- | --- |
| Intact cells (control) | 0.11 |
| + DCMU ($10^{-5}$ M) | 0.10 |
| + DBMIB ($10^{-5}$ M) | 0.005 |
| Broken cells | 0.1 |
| + DCMU ($10^{-5}$ M) | 0.11 |
| + DBMIB ($10^{-5}$ M) | 0.006 |
| + DCPIP ($10^{-4}$ M) | 0.003 |
| + sulfo-DSPD ($10^{-4}$ M) | 0.003 |
| + α-PetF-antibody (1:1000) | 0.008 |

Hydrogenase activity was dramatically reduced (up to 30-fold) by the ferredoxin antagonist sulfo-DSPD (Table II). Similar results were achieved with α-PetF-antibodies that specifically recognize the ferredoxin protein. In both cases, the hydrogenase enzyme cannot evolve hydrogen, thus demonstrating the role of ferredoxin as the obligatory donor for the hydrogenase reaction.

The electron transfer properties of different plant-type ferredoxins were measured in vitro with dithionite as a reducing reagent. The ferredoxin proteins of spinach, C. reinhardtii and S. obliquus were comparable regarding their capability to reduce purified S. obliquus hydrogenase. In this assay, $H_2$-evolving activities of 420, 390 and 350 U/mg protein with S. obliquus, C. reinhardtii and spinach ferredoxin, respectively, were observed. No hydrogen production could be measured with other possible electron donors like cytochrome and NADPH. In D. desulfuricans, the Fe-hydrogenase has been reported to catalyze both hydrogen production and uptake with low potential multi-heme cytochromes such as cytochrome $c_3$.

Molecular Characterization of hdyA Encoding a Fe-Hydrogenase

In order to isolate the gene encoding a Fe-hydrogenase in S. obliquus, polyA$^+$ RNA was isolated from cell cultures after one hour of anaerobic adaptation. Isolated RNA was transcribed and amplified by RT-PCR using oligonucleotides derived from conserved regions within the C. reinhardtii HydA gene (Happe, unpublished results). The complete cDNA clone of 2609 bp was obtained by 5'- and 3'-RACE PCR. It contains an open reading frame of 1344 bp encoding a polypetide of 448 amino acids (FIG. 1) followed by an extensive 3' UTR of about 1100 bp. The coding region of S. obliquus hydA exhibits features common to other green algae such as high GC content (64.2%) and a characteristic putative polyadenylation signal, TGTAA, 15 bp: upstream of the polyA$^+$ sequence.

In order to examine the exon-intron structure and the promoter region of the hydA gene, about 5 kb of the genomic DNA from S. obliquus were sequenced. The gene comprises 5 introns with a total size of 1310 bp (FIG. 1) whose 5'- and 3'-end contain typical plant splice donor and acceptor sites that follow the GT/AG rule. In FIG. 1, which is a schematic representation of S. obliquus hydA genomic and cDNA structures, the coding region of the hydA cDNA is illustrated as a large arrow with the transit peptide shown in black. The untranslated 59 and 39 sequences are marked as lines. The arrows below indicate the sequencing strategy; each arrow represents an independent sequence determination. TSP, transcription start point; ATG, start codon. The mosaic structure of hydA is indicated by gray (exons) and white (introns) boxes. The S2 probe and different restriction enzymes that were used in the Southern blot experiments are indicated on the figure.

A genomic southern blot was probed with a 750 bp PCR fragment to determine the copy number of the hydA gene. Single bands were observed in lanes with samples digested with HincII, EcORV and NdeI and a double band in the lane containing genomic DNA digested with SacI. The band migration positions matched the sizes predicted from the sequence of the hydA gene, indicating that HydA is encoded by a single copy gene. The same hybridization pattern was observed even under low stringency conditions (hybridization temperature 50° C.; data not shown). The transcription start position was determined by primer extension using RACE-PCR and was found 139 bp upstream of the ATG start codon. Several primers within 100 bp of the 5'-end of the known hydA cDNA were designed to confirm the accuracy of the transcription initiation site. All of the sequenced PCR clones had the same 5'-ends at position +1. As described for other green algae genes, a highly conserved TATA box element upstream of the transcription start point is absent (see, for example: C. D. Siflow in: *The Molecular Biology of Chloroplasts and Mitochondria in Chlamydomonas*, pp 25–40, (J. D. Goldschmidt-Clermont et al., eds.) Kluwer Academic Publishers, Dorecht, The Netherlands (1998)). However, the TACATAT motive at position −25 in a GC rich region shows similarities to other TATA motives in C. reinhardtii and therefore might be involved in gene expression.

HydA is a Novel Type of Fe-Hydrogenase

The polypeptide derived from the cDNA sequence has a length of 448 amino acids and a predicted molecular mass of 48.5 kDa (44.5 kDa excluding the transit peptide); consequently HydA is the smallest hydrogenase protein known so far. The N-terminus of HydA is basic and contains numerous hydroxylated amino acids and a Val-X-Ala motive at position 35, a characteristic feature of chloroplast transit peptides. The processed HydA protein is compared with four bacterial and two eukaryotic Fe-hydrogenases as shown in FIG. 2. FIG. 2 is a comparison of the S. obliquus-derived iron hydrogenase amino acid sequence with HydA sequences derived from other organisms. In FIG. 2, the protein alignment was done by using the Vector NTI program (InforMax). White letters with black background indicate amino acids identical to the HydA protein. Black letters with gray background indicate conserved changes of the amino acids. S. o., S. obliquus (this work); M. e., Megasphaera elsdenii; D. d., D. desulricans; T. v., Trichomonas vaginalis; C. p., C. pasteurianum; T. m., T. maritima; N. o., N. ovalis.

The homology in the carboxy-terminal region of all proteins is quite striking. For example, the S. obliquus HydA protein shows 44% identity and 57% similarity to the C. pasteurianum Fe-hydrogenase. The H-cluster in S. obliquus might be coordinated by four cysteine residues at positions 120, 175, 335, and 340. Other strictly conserved amino acid structures such as FTSCCPGW (334–350), TGGVMEAALR (474–483) and MACPGGCXXGGGQP (586–589) probably define a pocket surrounding the active center as shown by the structural data of C. pasteurianum and D. desulfuricans. On the other hand, the N-terminal region is completely different from all other Fe-hydrogenases. The protein sequences of the other enzymes comprise at least two [4Fe-4S] ferredoxin-like domains (called "f-cluster") which are necessary for the electron transport from the electron donor to the catalytic center. The Fe-hydrogenases of C. pasteurianum, Thermotoga maritima and Nyctotherus ovalis contain an extra [4fe-4S] cluster and one [2Fe-2S] center. This N-terminal domain with the F-cluster or other [Fe-S] centers is completely lacking in HydA of S. obliquus. This indicates that there is a direct electron transport pathway from the exogenous donor to the H-cluster.

To verify that the isolated cDNA encodes a Fe-hydrogenase, the hydA clone was expressed in the heterologous system E. coli. One band of recombinant HydA was observed on SDS-PAGE at approximately 44 kDa, in agreement with the molecular mass of the polypetide predicted from the cDNA sequence. Antibodies raised against the HydA protein of the C. reinhardtii, which cross-react with other Fe-hydrogenases but not with NiFe-hydrogenases (data not shown), were applied in Western blot analysis. One distinct signal with the over-expressed HydA protein of S. obliquus was obtained. The lysate of induced E. coli cells exhibited no hydrogenase activity. This result corresponds to observations by Voordouw et al. (*Eur. J. Biochem.*, 162, 31–36 (1987)) and Stokkermans et al. (*FEMS Microbiol. Lett.*, 49, 217–222 (1989)) who also detected no $H_2$-production of recombinant Fe-hydrogenases in E. coli cells. The reason for that might be that the bacterial cells do not have the ability to assemble the special H-cluster of the Fe-hydrogenases.

Rapid Induction of hydA mRNA During Anaerobic Adaptation

The regulation of the hydA gene expression was examined by Northern blot analysis and reverse transcription-PCR (RT-PCR). Aerobically grown cells of S. obliquus did not show a hydrogenase activity. Total RNA and mRNA were isolated from cells which were induced by argon bubbling for 0, 1 and 4 hours. Northern blot analysis and RT-PCR demonstrated that the hydA gene is expressed after anaerobic adaptation. There is a very weak signal without adaptation (t=0), but strong signals of the transcript could be detected after anaerobic induction. The full length of the hydA cDNA clone was confirmed by the transcript signal (2.6 kb) on the Northern blot.

Discussion

In green algae, the occurrence of a hydrogen metabolism induced by anaerobic conditions is well established. Despite the great interest in hydrogen evolution for practical applications ("biophotolysis"), the hydrogenase genes from green algae have heretofore not been isolated. The hydA gene and the HydA protein of Scenedemus obliquus presented herein belong to the class of Fe-hydrogenases.

Fe-hydrogenases have been isolated only from certain anaerobic bacteria and some anaerobic eukaryotes as well as from the anaerobically adapted green alga C. reinhardtii (T. Happe et al., Eur. J. Biochem. 214, 475–481 (1993)). The enzymes are found to exist in monomeric, dimeric and multimeric forms; however, in eukaryotes, only monomeric proteins have been isolated.

The HydA protein of S. obliquus is synthesized in the cytoplasm. The first 35 residues $M^1$ to $A^{35}$) of the amino acid sequence derived from the cDNA sequence are supposed to function as a short transit peptide which routes the nuclear encoded protein to the chloroplast. Several positively charged amino acids which describe a typical feature for algal transit peptides are found in HydA. The three terminal residues of the signal sequence, Val-X-Ala, constitute the consensus for stromal peptidases.

The hydrogenase of S. obliquus represents a novel type of Fe-hydrogenase. The monomeric enzyme of 448 amino acids and a calculated molecular mass of 44.5 kDA for the processed protein is the smallest Fe-hydrogenase isolate so far. The protein sequence consists of an unusual N-terminal domain and a large carboxyterminal domain containing the catalytic site. The structurally important C-terminus of the S. obliquus HydA sequence is very similar to that of other Fe-hydrogenases. Four cysteine residues at positions $C^{120}$, $C^{175}$, $C^{336}$ and $C^{340}$ coordinate the special [6Fe] cluster (H-cluster) of the active site. A number of addition residues define the environment of the catalytic center. Peters et al. postulated twelve amino acids in C. pasteurianum to form a hydrophobic pocket around the cofactor (Science, 282, 1853–1858 (1998)). Ten residues are strictly conserved while two amino acids vary within the Fe-hydrogenase family ($S^{232}$, $I^{268}$, in C. pasteurianum, $A^{119}$, $T^{155}$ in T. vaginalis and $A^{44}$, $T^{80}$ in S. obliquus). A small insertion of 16 amino acids is noted in S. obliquus but this addition occurs in an external loop of the protein and probably has no special function.

Figure 3:
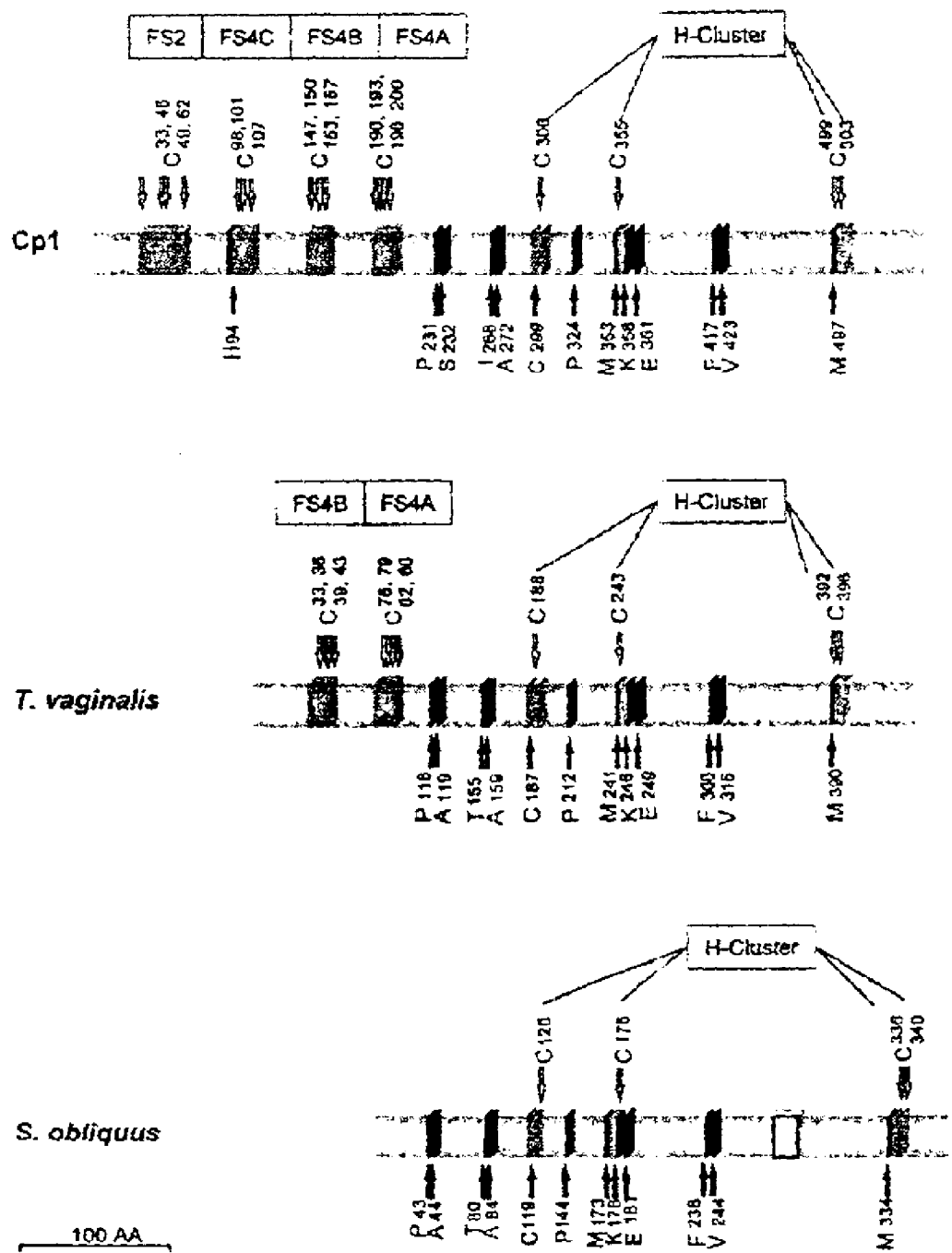
FIG. 3 is a schematic diagram showing the conserved cysteine residues and other important amino acids of the H cluster

Until now, all Fe-hydrogenases possess a ferredoxin-like domain in the N-terminus coordinating two [4Fe4S] clusters (FS4A, FS4B, as shown in FIG. 3. FIG. 3 is a schematic diagram showing the conserved cysteine residues and other important amino acids of the H cluster. In FIG. 3, the protein is illustrated as a large gray arrow. Small arrows indicate parallelograms which demonstrate conserved amino acids in the protein. Cysteines participating at the coordination of the [Fe-S] clusters are gray, whereas identical amino acids are black. An insertion of 16 amino acids in the S. obliquus protein is illustrated as a spotted bar. FS4 indicates the [4Fe-4S] cluster; and FS2 indicates the [2Fe-2S] cluster.

The iron sulfur cluster facilitates the transfer of electrons between external electron donors or acceptors and the H-cluster. The N-terminus of the S. obliquus protein is strongly reduced compared to other Fe-hydrogenases and no conserved cysteines are found. Therefore it is postulated that all accessory Fe-S clusters (FS2, FS4A, FS4B, FS4C) are missing. No indication of a second subunit has been observed during purification of the protein.

In contrast to earlier observations in S. obliquus, the present inventor could neither detect the postulated two subunits of a potential NiFe-hydrogenase, nor could he find a Ni-dependency related to the hydrogenase activity. Francis reported about two forms of hydrogenases in S. obliquus (Photosynthetica, 23, 43–48 (1989)), but although the present inventor used the same alga strain and identical adaptation conditions, a second hydrogenase activity was not detected during the purification steps.

Physiological studies by others have shown that the hydrogen evolution is coupled to the light reaction of the photosynthesis. In contrast to earlier observations in S. obliquus, the measurement of PSII independent $H^2$-production was not influenced by DCMU. The electrons required for $H^2$-evolution come from redox equivalents of the fermentative metabolism and are supplied into the photosynthetic electron transport chain via the plastochinone pool.

For the first time, it is demonstrated that the ferredoxin PetF functions as the in vivo electron donor of the Fe-hydrogenase from S. obliquus. Hydrogenase activity can be specifically blocked by addition of the ferredoxin antagonist sulfo-DSPD (A. Trebst, J Methods Enzymol., 69, 675–715 (1980)) and antibodies raised against the PetF protein. In vitro, a hydrogen evolution by HydA was only measured with plant-type [2Fw-2S] ferredoxins like PetF of S. obliquus, C. reinhardtii and spinach as electron mediators. Bacterial Fe-hydrogenases are known to be reduced by [4Fe4S] ferredoxins and do not accept electrons from plant-type proteins (J. M. Moulis et al., Biochemistry, 34, 16781–16788 (1995)).

Figure 4:
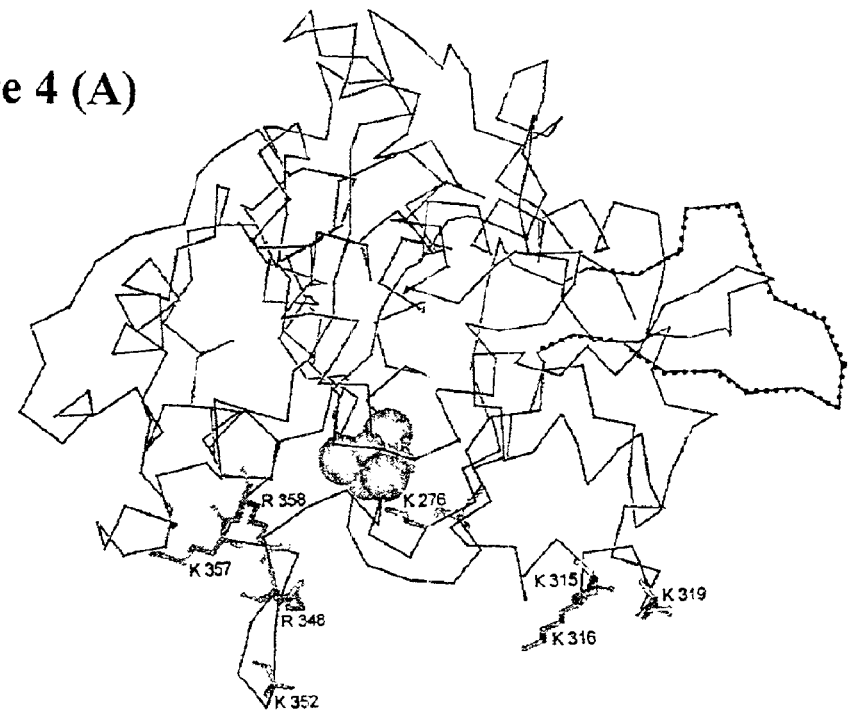
FIG. 4(A) is a schematic view of the structure of *S. obliquus* HydA.
FIG. 4(B) is a schematic view of the *S. obliquus* electron donor ferredoxin.
Figure 4:
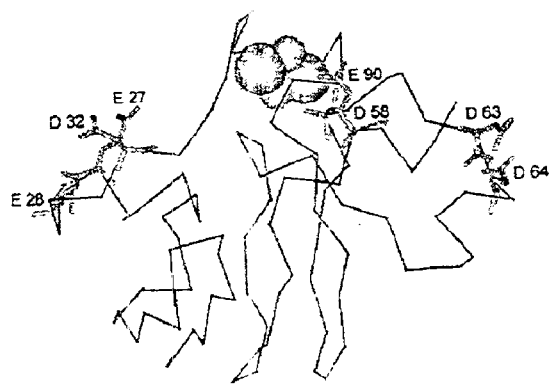

The analysis of the 3D-structure of the Fe-hydrogenase from C. pasteurianum (CpI) gave evidence that the interaction with external electron donors might occur at the accessory [Fe-S] clusters in the N-terminal domain (J. W. Peters, Curr. Opin. Struct. Biol., 9, 670–676 (1999)). Based on the X-ray structure of CpI (N. Guex et al., Trends Biochem. Sci., 24, 364–367 (1999), the Fe-hydrogenase of S. obliquus was modeled. FIG. 4 is a Schematic view of the structures of S. obliquus HydA (A), and the electron donor ferredoxin (B). The figure shows the α carbons and the side chains of charged residues that might be important for the electron transfer reaction or the interaction between HydA and the ferredoxin from S. vacuolatus. The 16-amino acid insertion of the hydrogenase appears as external loop and is distinguished as a dotted line. The amino acid sequence of the mature HydA protein (His 19-Tyr 404) was submitted to the SWISS-MODEL server. The present inventor generated a model of HydA with the known three-dimensional structure of the iron hydrogenase from C. pasteurianum as template, sharing 57% sequence identity with the submitted sequence. The Protein Data Bank file was visualized by the Swiss-PDB viewer !(J. M. Moulis, Biochemistry, 34, 16781–16788 (1995)). As shown in FIG. 4, a region of positive surface potential is observed within HydA based on a local concentration of basic residues. In contrast to the docking position of ferredoxin in CpI, these charged amino acids in the *S. obliquus* Fe-hydrogenase are located within the C-terminal domain, forming a niche for electron donor fixation.

The known alga ferredoxin proteins exhibit high degrees of sequence identity (over 85%) and the charged amino acids are strictly conserved. The petF sequence of *S. obliquus* is unknown, but very recently the X-ray model of the ferredoxin from another *Scenedesmus* species (*Scenedesmus vacuolatus*) was published (M. T. Bes et al., *Structure*, 7, 1201–1213 (1999)). The structure revealed negatively charged amino acids like aspartate and glutamate near the [2Fe-2S] cluster. The [Fe-S] center and the H-cluster of the hydrogenase probably come into close proximity through electrostatic interactions. This geometry is consistent with efficient electron transfer among these prosthetic groups.

As already shown in various studies, a correlation exists between the duration of time of the anaerobic adaptation and increase of hydrogen production. RT-PCR and Northern blot analyses with mRNA of aerobic and anaerobically adapted cells from *S. obliquus* showed an increased level of hydA transcript after one hour of induction. Correspondingly, hydrogen evolution was only measured after a short time anaerobic adaptation. These results suggest that the expression of the hydA gene is regulated at the transcriptional level. The small amount of transcript that was detected at t=0 may be due to transcript analysis induced by microanaerobic conditions during the RNA isolation procedure. Alternatively, a low level of hydA transcript might be constitutively present in the cell and is only drastically increased after anaerobic adaptation.

The foregoing discloses a monomeric enzyme, iron hydrogenase (HydA), having a molecular mass of 44.5 kDa. (exclusive of the transit peptide associated therewith) derived from *Scenedesmus obliquus*. The polypeptide derived from the cDNA sequence, set forth herein as SEQ. ID. NO. 4, has a length of 448 amino acids and is the smallest hydrogenase described to date. The nucleic acid sequence coding HydA in *Scenedesmus obliquus* is set forth in SEQ. ID. NO. 1 appended hereto, and the cDNA sequence is set forth as SEQ. ID. NO. 7.

In addition to the unicellular green algae *Scenedesmus obliquus*, discussed above, other algae within the order of Chlorophyta (e.g. *Chlamydomonas reinhardtii* and *Chlorella fusca*) contain a gene (hydA) coding for a novel iron-hydrogenase enzyme (HydA) as will be discussed below. This gene, through its encoded enzyme, catalyzes the synthesis of molecular hydrogen from protons and high potential energy electrons, and releases significant amounts of hydrogen gas, which is a valuable and clean source of energy. As with *Scenedesmus obliquus*, the process of $H_2$-production entails the utilization of sunlight and the oxidation of water or organic substrate in photosynthesis to generate reduced ferredoxin, which is the carrier of the high potential energy electrons. The isolation, sequencing and characterization of the hydA genomic DNA, cDNA, precursor and mature iron-hydrogenase of two additional photosynthetic eukaryotes which may be used for hydrogen gas production is disclosed below.

II. *Chlamydomonas reinhardtii*
*C. reinhardtii* Algal Strains and Growth Conditions Wild-type *C. reinhardtii* 137c(mt+) strain was originally obtained from the *Chlamydomonas* Culture Collection at Duke University. The stain was cultured photoheterotrophically in batch cultures at 25° C. under continuous irradiance of 150 $\mu$mol photons per square meter per second. Cultures containing TAP (Tris acetate phosphate) medium were flushed vigorously with air supplemented with 5% $CO_2$. Cells were collected by centrifugation (8 minutes @ 5000 g) in the mid-exponential growth stage (1–2×10$^6$ cells per ml). After harvesting the cells in the id-exponential stage of growth, the pellet was resuspended in 0.02 vol. of fresh TAP medium. The algae were anaerobically adapted by flushing the culture with argon in the dark.

Hydrogen Evolution Assay

Hydrogenase activity of *C. reinhardtii* was determined in vitro with reduced methyl viologen using a gas chromatograph (Hewlett Packard 5890 Å Series II, column: molecular Sieve 5 Å, Mesh 60/80). The assay, containing in a final volume of 2 mL Pipes pH 6.8 (20 mM), $Na_2S_2O_4$ (20 mM), MV (5 mM), was incubated anaerobically at 25° C. for 20 min. One unit is defined as he amount of hydrogenase evolving 1 $\mu$mol H2 per minute.

Purification of the Fe-hydrogenase and Amino Acid Sequence

Cells from a 40-L culture of *C. reinhardtii* were harvested by ultra filtration through an Amicon Ultrafiltration System DC 10 LA, with a hollow-fiber filter. The pellet was resuspended in 200 mL TAP medium. After anaerobic adaptation by flushing the solution with argon for 1 h in the dark, all steps were performed under strictly anaerobic conditions. The isolated Fe-hyrogenase was chemically cleaved by cyanogen bromide (CNBr). After separation of he CNBr fragments on an SDS polyacrylamide gel, four peptides were blotted onto a poly(vinylidene difluoride) membrane and were sequenced. Automated Edman degradation was performed with an Applied Biosystem model 477 A sequencer with online analysator model 120 A.

RNA Blot Hybridization

Total nucleic acids were isolated from algae grown under aerobic conditions and after anaerobic adaptation. Poly(A)+ RNA was isolated using the RNA Kit (Qiagen); 10 $\mu$g total RNA or 0.5 $\mu$g poly(A)+ RNA were separated on each lane of 1.2% agarose gels in formaldehyde. The RNA was transferred to n ion membranes (Hybond+, Amersham) and hybridized with RNA probes, which were labeled with digoxygenin (DIG)-dUTP by in vitro transcription. Transcripts of the hydA gene were detected using a 1.0-kb Sma I cDNA fragment. A DIG-dUTP labeled cDNA, which encodes the malate dehydrogenase, was used as a control for a constitutive express gene. FIG. 5(A) shows the structural features of the HydA cDNA. Coding regions are marked as large arrows with the transit peptide shown in black. Lines indicate 5' and 3 URT's. In FIG. 5(B), the mosaic structure of HydA is illustrated by gray (exons) and white (introns) boxes. The RNA and DNA probes that were used for blotting are as noted on the figure.

Suppression Subtractive Hybridization (SSH)

SSH was performed with the Clontech P WR-select4 cDNA Subtraction Kit (Clontech Laboratories Inc., Palo Alto, Calif., USA.) according to the manufacturer's recommendations, except for modifications of th PCR and hybridization conditions. The mRNA was isolated from aerobically grown cells (driver) and from anaerobically adapted algae (tester). The driver and tester cDNAs were denatured separately for the first hybridization at 100° C. for 30 s and then incubated for 10 h a 68° C. For the second hybridization, driver cDNA was denatured at 100° C. for 30 s, then directly added to the pooled mix of the previous hybridization, and incubated at 68° C. for 20 h. Primary and secondary PCR conditions were altered to increase the specificity of the amplification. The PCR conditions with subtracted cDNA were as follows: 25 cycles each 94° C. for 30 s, 68° C. for 30 s, and 72° C. for 1 min. The subtracted cDNA was subjected to a second round of nested PCR, using the same PCR conditions with a decreased number of 15 cycles. Specific primers were used for the identification of the amplified HydA cDNA fragment. From the N-terminal amino-acid sequence, a degenerate oligonucleotide Hyd5 [5'-GCCGCCCC(GC)GC(GCT)GC(GCT)GA(AG)GC-3'] was synthesized, thing into account known C.reinhardtii amino-acid sequences. The second primer, Hyd2 (5'-CCAACCAGGGCAGCAGCTGGTGAA-3'), was deduced from the conservative amino acid sequence motif of Fe-hydrogenases FTSCCP.

PCR was performed using either Hyd5 or Hyd2 and the nested PCR primer 2R from the Clontech Subtraction Kit. The PCR conditions were as follows: 20 pmol per ml of each primer were used; 35 cycles (denaturing at 95° C. for 40s, annealing at 54° C. for 1 min, and extension at 72° C. for 1 min). The amplified cDNA fragments were cloned into the T overhang vector pGEM®-T Easy (Promega).

Screening of the cDNA Library, Cloning and Sequencing

A cDNA library was constructed using the Stratagene ZAP Express cDNA synthesis Kit (Stratagene, La Jolla, Calif., USA) with 5 µg mRNA of anaerobically adapted cells of C. reinhardtii. Double-stranded cDNA was ligated into the ZAP Express vector, packaged with the Gigapack Gold Kit, and transfected into Escherichia coli XL Blue MRF cells. The primary recombinant library contained $5 \times 10^6$ recombinant phages and was amplified according to the manufacturer's instructions.

A 366-bp PCR fragment was radiolabeled with [α-32P] dCTP using he random-primer method. Approximately $5 \times 10^5$ plaques were analyzed under stringent hybridization conditions, resulting in 20 positive signals. The pBK-CMV phagemid vector with the different cDNAs was excised and used as a template for PCR, which was performed by using Hyd2 and Hyd5 primers at an annealing temperature of 56° C. for 1 min. Four plasmids contained cDNA fragments that showed similarities to the 366-bp fragment. All cDNA fragments were partially sequenced, and the largest clone, pAK60, was completely sequenced. Sequencing was carried out by the dideoxy nucleotide triphosphate chain-termination method using the $T_7$ sequencing Kit (Pharmacia Biotech). Both strands of genomic and cDNA of hydA were completely sequenced using a nested set of unidirectional deletions or hydA specific synthetic oligonucleotides. The sequences of the Fe-hydrogenase are available under accession number CREO 12098.

Primer extension experiments were performed as described previously by the present inventor (J. Biol. Chem., 276, 6125–6132 (2001)) using a 22-mer oligonucleotide (5'-AATAGGTGGTGCGATGAAGGAG-3'), which is complementary to the 5' end of the hydA transcript.

Expression Studies in E. coli and Western Blot Analysis

The coding region of hydA was amplified by PCR The primers were identical to the cDNA sequences coding for he N-and the C-terminus of the mature protein plus several additional bases including NdeI and BamI restriction sites, respectively (underlined). The oligonucleotide sequences were: HydNde (5'-CATATGGCCGCACCCGCTGCGGAGGCGCCT-3'), HydBam (5'-CCGGATCCTCAAGCCTCTGGCGCTCCTCA-3').

The hydA gene, corresponding to amino acids 57–497, was amplified, confirmed by sequences analysis and cloned into corresponding sites of he pET9a expression vector (Promega). The constructed plasmid was then ransformed into E. coli strain BL21(DE3). After induction with 1 mM isopropyl-thio-β-D-galactoside, the cells were resuspended in lysis buffer. Crude extracts from C. reinhardtii were isolated by harvesting cells after indicated anaerobic adaptation times. The pellet was resuspended in solubilization buffer and incubated with vigorous vortexing at RT for 30 min. The protein extracts from C. reinhardtii and E. coli were separated by 12% SDS/PAGE and blotted onto a poly(vinylidenedifluoride) membrane. Affinity-purified antibodies were diluted 1:200 and used for Western blot analyses.

Sequence Analysis and Protein Modeling

Nucleic acid and protein sequences were analyzed with the programs SCI ED CENTRAL (Scientific Educational Software) and CLUSTALW. The BLAST server (Altschul et al., Nucleic Acid Res., 25, 3389–3402 (1985)) of the National Center for Biotechnology Information (Bethseda, Md., USA) was used for database searches.

Isolation of cDNA Clones, which are Differentially Expressed During Anaerobic Adaptation In order to amplify a part of the hydrogenase gene in a PCR reaction, degenerate oligonucleotides corresponding to conserved regions of known Fe-hydrogenases were used. All products of expected sizes were cloned and sequenced, but they showed no homologies to other hydrogenases (data not shown). Examinations were then focused on the process of anaerobic adaptation in C. reinhardtii, because the Fe-hydrogenase was only detected under these conditions. The present inventor isolated two different populations of mRNA and advantageously employed the SSH technique. Poly(A)+ RNA was isolated from aerobically grown C. reinhardtii cells and from a cell suspension flushed 15 min with argon. After cDNA synthesis, subtractive hybridization, and PCR experiments, the amplified PCR fragments were cloned and sequenced. Twenty different clones containing inserts of 184–438 bp were analyzed. In transcription analyses, 15 of them showed an increased signal under anaerobic conditions (data not shown). Database comparisons (using GenBank/EBI DataBank) confirmed that eight of these cDNA fragments are similar to genes encoding proteins of the cytoplasmic ribosome complex. The sequences of six clones did not correspond to any entries in the databases. Four of these novel clones showed differences in expression between aerobically grown and anaerobically adapted cultures. Another cDNA fragment indicated similarity to the 5' region of the Fe-hydrogenase from bacteria.

Analysis of the hydA cDNA and Genomic Sequences

A cDNA expression library was constructed using poly (A)+ RNA from anaerobically adapted cells (15 min). Two oligonucleotides were generated on he basis of the cDNA fragment isolated by SSH and the N-terminal sequences of the purified hydrogenase. They were used to amplify a 366-bp cDNA fragment that showed 41% identity to the corresponding part of the Fe-hydrogenase of C. pasteurianum. The fiagment was labeled with [α-$^{32}$P]dCTP and used to screen the cDNA library. Four independent cDNA clones with different sizes of 2.4-,1,9-, 1.7- and 1.6-kb were identified and sequenced. The nucleotide sequence of the largest clone, 2399-bp, revealed an ORF encoding a polypeptide of 497 amino acids. The cDNA also contained a 5'UTR (158-bp) and a longer 3'UTR (747-bp excluding the polyadenylated tail). Characteristic features of other C. renhardtii cDNA clones, e.g. a high average G/C content (62.1%)and a putative polyadenylation signal (TGTAA) 727-bp downstream of the stop codon were found. The transcription start position was confirmed by primer extension 158-bp upstream of the ATG start codon.

Figure 5:
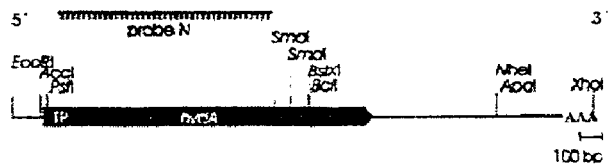
FIG. 5(A) is a schematic map of the cDNA and the genomic DNA region of HydA from *C. reinhardtii*.showing the structural features of the HydA cDNA. Coding regions are marked as large arrows with the transit peptide shown in black.lines indicate 5' and 3' URTs.
FIG. 5(B) is a schematic map of the cDNA and the genomic DNA region of HydA from *C.reinhardtii*.showing the structural features of the HydA cDNA.
Figure 5:
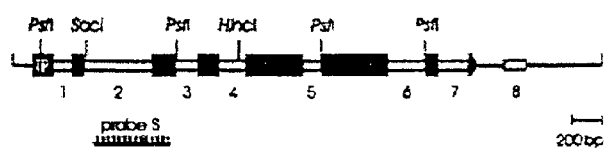

FIG. 5(A) is a schematic map of the cDNA and the genomic DNA region of HydA from C. reinhardtii.showing the structural features of the HydA cDNA. Coding regions are marked as large arrows with the transit peptide shown in black.lines indicate 5' and 3' URTs. FIG. 5(B) is a schematic map of the cDNA and the genomic DNA region of HydA from C. reinhardtii.showing the structural features of the HydA cDNA. In FIG. 5 (B), the mosaic structure of hydA is illustrated by gray (exons) and white (introns) boxes. The RNA and DNA probes that were used for the blotting experiments are noted on the Figure.

Approximately 5-kb of the hydA genomic region was determined. The coding sequence is interrupted by seven introns with sequences at their 5' and 3' ends, corresponding to the typical splicing sequences from eukaryotes as shown in FIG. 5B. The promoter region does not contain a putative TATA box or any other known transcription motifs. The sequence data were submitted to the GenBank/EBI Data-Bank under accession number CRE012098. In subsequent studies, parts of the cDNA sequence were determined by another group and deposited under accession number AF289201.

Southern hybridization experiments were performed at high stringency using a PCR fragment as probe. They showed the presence of one hybridizing signal of similar intensity in different digestions, suggesting that HydA is encoded by a single copy gene in the C. reinhardtii genome. The same hybridization pattern was observed even under low stringency conditions (hybridization temperature 50° C.; data not shown).

Characterization of the Fe-Hydrogenase HydA from C. reinhardtii

The mature polypeptide consists of 441 amino acids with a calculated molecular mass of 47.5 kDa and a predicted isoelectric point of 5.6. The N-terminal 56 amino acids probably function as a transit peptide, because they show characteristics of polypeptides that route proteins into the chloroplast stroma. The stromal targeting domain is most likely cleaved by a stromal peptidase at the conserved cleavage motive Val-Ala-Cys-Ala. In addition to the detection of the protein using antibodies raised against the Fe-hydrogenase, the localization of the mature protein in the chloroplast stroma is indicated by a high content of hydroxylated and basic amino acids in the transit peptide sequence.

The deduced amino-acid sequence of he mature HydA polypeptide from C. reinhardtii shows 60% identity and 71% similarity to the Fe-hydrogenase of S.obliquus, Comparisons with NiFe-hydrogenases of bacteria (including the photosynthetic cyanobacteria) had obviously lower scores, e.g. 25% similarity with the NiFe-hydrogenase (HoxH) of Ralstonia eutropha. A conserved domain of about 300 amino acids is found in the C-terminal part of all Fe-hydrogenases. The sequences are highly conserved, especially in the region that is involved in the catalytic mechanism (H-cluster), indicating structural similarity between Fe-hydrogenases. Four cysteine residues at positions 114, 169, 361 and 365 might coordinate the H-cluster in C. reinhardtii. Twelve strictly conserved amino acids of HydA proteins probably define a binding pocket surrounding the active center as shown by structural data reported by others for C. pasteurianum and D. desulficans iron hydrogenase. All of them are present in the C. reinhardtii protein (Pro37, Ala38, Thr74, Ala78, Cys113, Pro138, Met167, Lys172, Glu175, Phe234, Val240 and Met359). An interesting insertion of 45 amino acids was only identified at the C-terminus of the C.reinhardtii polypeptide (position 285.329).

The N-terminal region of the green algae protein is much shorter and completely different than all known Fe-hydrogenases. Amino-acid sequence analyses have indicated that Fe-hydrogenases, in general, contain two [4Fe)4S] clusters (F-cluster) in a ferredoxin-like domain. They might be involved in the transfer of electrons from the donor to the catalytic center. This N-terminal domain with the F-cluster or other conserved cysteines is completely missing in HydA of C. reinhardtii. A novel electron transport pathway is postulated from the exogenous donor (ferredoxin) directly to the H-cluster.

Protein Sequencing of the Enzyme and Recombinant Expression of HydA in E. coli

Figure 6:
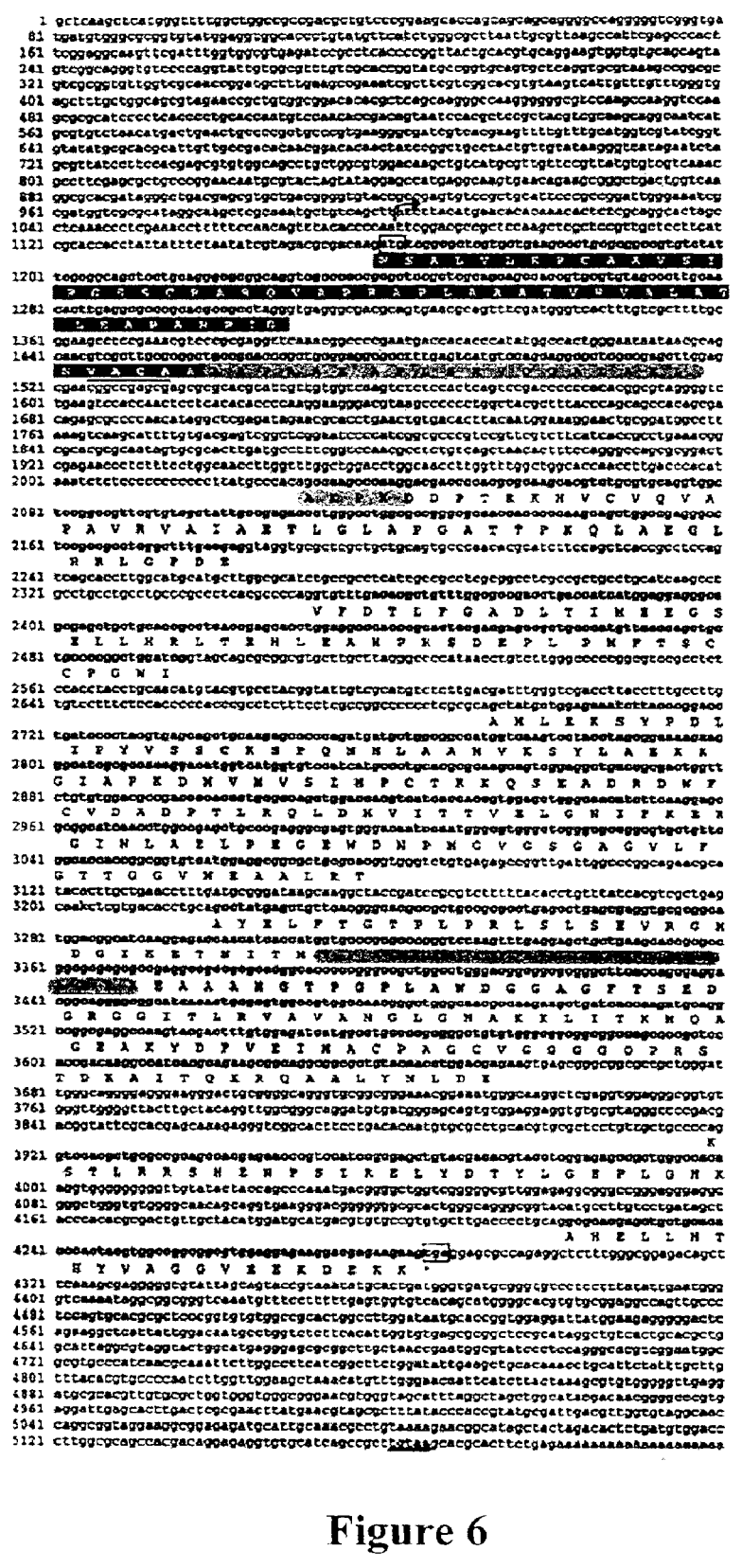

To verify that the hydA ORF encodes the Fe-hydrogenase of C. reinhardtii, the enzyme was purified according to Happe and Naber (Eur. J. Biochem. 214,475–481 (1993)). The purified protein was able to evolve hydrogen, when incubated with reduced methyl viologen. After proteolytic digestion with cyanogen bromide, four bands of 4, 8, 9 and 11 kDa were detected after SDSlPAGE separation (data not shown). Two fragments (9 and 11 kDa) were sequenced by Edman degradation. FIG. 6 shows the nucleotide sequence of the hydA cDNA and the deduced amino acid sequence of the hydrogenase from C. reinhardtii. The two fragment sequences are identical with he deduced amino-acid sequence of hydA (sequences are shadowed in gray in FIG. 6). The fragment corresponding to the cDNA region between 158 and 1636 bp of hydA was NdeI-BamHI cloned into the expression vector pET9a. The heterologous expressed protein was detected using antibodies raised against the Fe-hydrogenase. Both the purified Fe-hydrogenase of C. reinhardtii and the overexpressed enzyme had the same size (47.5 kDa). No hydrogenase activity could be measured within the lysate of the induced E. coli cells. This result is in agreement with Stokkermans et al. and Voordouw et at. (ibid) who also detected no $H_2$-production of the recombinant expressed Fe-hydrogenase from Desulfovibrio vulgaris in E. coli cells. An explanation might be the inability of E. coli to assemble the unique active site of the Fe-hydrogenases. It is known that E. coli has only three NiFe-hydrogenases with a different maturation system for the catalytic center.

FIG. 6 shows the nucleotide sequence of the hydA cDNA and the deduced amino acid sequence of the hydrogenase from C. reinhardtii. The sequence was submitted to the GenBank/EBI Data Bank under accession number CRE012098. A curved arrow marks the transcription start point. The ATG start codon and the TGA stop codon are drawn in boxes. Boldface letters indicate the cDNA sequence. Gray shadows mark amino acids corresponding to polypeptide sequences that were determined by sequencing the N-terminus of the protein. Black shadows mark the putative transit peptide, and the underlined amino acids indicate the putative cleavage site for the endopeptidase. Boldface double underlined letters indicate a signal for polyadenylation.

Induction of Gene Expression During Anaerobic Adaptation

In aerobically grown cells, neither hydrogenase activity nor protein can be identified by immunoblot analysis. However, HydA can be detected only 15 min after anaerobic adaptation. The expression of the hydA gene is probably regulated at the transcriptional level. Total RNA was isolated from cells that had been anaerobically adapted by flushing with argon for 0,15, and 30 min. Northern blot hybridization demonstrated that the hydA gene is expressed very rapidly after the beginning of anaerobic adaptation. No transcript could be detected before adaptation (t=0), but a significant signal occurred after just 15 min of anaerobiosis. The size of the transcripts (2.4 kb) confirmed the full-length of the isolated hydA cDNA fragment.

Differentially Expressed Genes During Anaerobic Adaptation

In the light, algae degrade cellular starch via glycolysis and hydrogen gas is evolved. It has been suggested that reducing equivalents from the glycolysis or the citric acid cycle can transfer their electrons to the photosynthetic electron transport chain (M. Gibbs et al., *Plant Physiol.* 82, 160166 (1986)). However, the molecular principles of the gene induction under anaerobic conditions in *C. reinhardtii* are poorly understood.

The present inventor has investigated the patterns of gene expression in aerobically grown and anaerobically adapted cells by isolating differentially expressed genes. The SSH method combines subtractive hybridization with PCR to generate a population of PCR fragments enriched with gene sequences that are only expressed under anaerobic conditions. Compared to other PCR-based cloning strategies, such as differential display, the great advantage of SSH is that fewer false positives are generated; 70% of the cloned fragments represented differentially expressed genes.

Among the 20 sequenced cDNA clones, three DNA fragments encoding the ribosomal S8 protein were found. Most of the other sequences (eight of 20) also corresponded to ribosomal protein sequences. This might indicate that the transcripts of the ribosomal protein genes (rps, rpl) accumulate under stress conditions. This is in good agreement.with Dumont et al. (*Plant Sci.*, 89, 55–67 (1993)) who found that an accumulation of ribosomal proteins takes place under phosphate starvation. Moreover, two of the identified cDNAs encode for proteins, (aldolase, enolase), which are induced in other organisms by anaerobic stress. Anaerobic treatment of maize seedlings alters he profile of total protein synthesis. It is known that the induction of the anaerobic proteins is the result of an increased mRNA level. Maize (*Zea mays* L.) responds to anaerobic stress by redirecting the synthetic machinery towards the synthesis of some enzymes involved in glycolysis or sugar-phosphate metabolism.

C. reinhardtii HydA Belongs to a New Class of Fehydrogenases

HydA of *C. reinhardtii*, the first isolated gene encoding a hydrogenase of a photosynthetic eukaryotic cell, represents a novel type of Fe-hydrogenases. Parts of the deduced amino-acid sequence of the cDNA correspond to the polypeptide sequence of the tryptic fragment (VPAPGSKFEELLKHRAAARA), and the N-terminus (AAPAAAEAPLSHVQQALAELAKPKD) from the purified native enzyme. Further evidence that the isolated cDNA encodes an Fe-hydrogenase is the fact that the recombinant HydA specifically reacts with the antibodies raised against the active enzyme. The amino-acid sequence of HydA shows only considerable similarity to Fe-hydrogenases but not to NiFe-hydrogenases. The Fe-hydrogenase family is one class of hydrogenases defined by Vignais et al. (*FEMS Microbiol. Rev.* 25, 455–501 (2001)). The enzymes have been identified in a small group of anaerobic microbes, where they often catalyze the reduction of protons with a high specific activity to yield hydrogen. Interestingly, Fe-hydrogenases were not found in cyanobacteria, the free-living ancestor of plastids, suggesting a noncyanobacterial origin for the algal hydrogenases.

The important structural features found among the amino-acid sequences of Fe-hydrogenases are also present in the *C. reinhardtii* hydrogenase sequence. A highly conserved domain of about 130 amino acids was detected in the C-terminal part of the protein. The designated active site domain consists of an atypical [Fe-S] cluster (H-cluster). In *C. pasteurianum*, the H-cluster contains six Fe atoms arranged as a [4Fe-4S] subcluster bridged to a [2Fe] subdluster by a single cysteinyl sulfur. The [4Fe-4S] subcluster is coordinated to the protein by four cysteine ligands, which have also been found in the amino acid sequence of *C. reinhardiii*. A number of mostly hydrophobic amino acid residues define the environment of the active site and might have a function in protecting the H-cluster from solvent access. In contrast to all Fe-hydrogenases, including HydA of *S. obliquus*, the enzyme of *C. reinhardtii* has an interesting additional 18 protein domain. A small insertion of 45 amino acids between residue Ser284 and Val330builds an external loop of the protein that might be involved in electrostatic binding of the natural electron donor ferredoxin (Happe et al., unpublished results)

In the N-terminus of other Fe-hydrogenases, further cysteine residues were found that bind accessory iron sulfur clusters. Others have shown that a ferredoxin homologous domain (F-cluster) coordinates two [4FeAS] clusters in all non-algal Fe-hydrogenases. An additional [4Fe-4S] cluster and one [2Fe-2S] center were detected within the Fe-hydrogenases of *C. pasteurianum* (Peters et al., *Science*, 282, 1853–1858 (1998)). Based on similarities of the primary sequences, the same cofactors are proposed for *Thermotoga maritime* (A. Akhmanova et al., *Nature*, 396, 527–528 (1998)) and *Nyctotherus ovalis* (J. Meyer et al., *Biochim. Biophys. Acta*, 1412, 212–229 (1999)). The F-cluster is responsible for the electron transfer from the electron donor (mostly ferredoxin) to the active center. It has been suggested by Vignais et al. (*FEMS Microbiol. Rev.*, 25, 455–501 (2001)) that the proteins containing two F-clusters are ancestors of the Fe-hydrogenases.

The N-terminus of the *C. reinhardtii* and *S. obliquus* proteins is strongly reduced, and conserved cysteines were also not found. Therefore it is suggested that all accessory [Fe-S] clusters are missing in the algal hydrogenases. The native protein of *C. reinhardtii* is located in the chloroplast stroma. The first 56 amino acids of the unprocessed enzyme probably function as a transit peptide, because they were not characterized in the purified hydrogenase and a putative peptidase cleavage site (Val-Ala-Cys-Ala) could be detected at the end of this fragment.

The natural electron donor of the hydrogenase in *C. reinhardtii* is the ferredoxin (PetF) of the photosynthetic electron ransport pathway. Measuring the $H_2$-evolution, it has been found that the hydrogenase activity is directly linked to the 47.5 kDa subunit. As a second subunit necessary for hydrogenase activity has not been found, it is suggested that a direct electron transfer from PetF to HydA takes place. In vitro, a hydrogen evolution by HydA was only measured with plant-type [2Fe-2S] ferredoxins such as PetF of *C. reinhardtii*, *S. obliquus* and spinach as electron mediators (data not shown).

Figure 7:
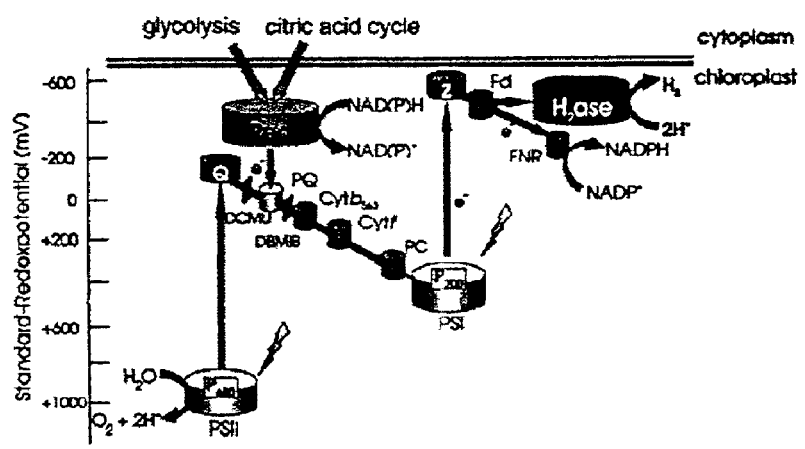
FIG. 7 is a schematic diagram showing the light-dependent photoevolution of hydrogen in green algae.

FIG. 7 is a schematic diagram illustrating the light-dependent photoevolution of hydrogen in green algae. The electrons for hydrogen evolution are fed into the photosynthetic electron transport chain either via PS II or via the plastoquinone pool after oxidation of reducing equivalents. The natural electron donor, PetF, transfers the electrons from PS I to the hydrogenase.

The most likely explanation for photosynthetic green algae retaining the anaerobically induced hydrogenases is that the enzymes ensure the survival of the ceus under anaerobic conditions. Melis et al. have shown that $H_2$-evolution is the only mechanism available to the algae for generating sufficient amounts of ATP under S-depleted anaerobic conditions. It is known that *C. reinhardtii* is still able to photoproduce hydrogen when photosystem II is inhibited by DCMU, but no H$_2$-evolution occurs after an addition of 2,5-dibromo-3-methyl-6-isopropyl-p-benzochinon (DBMIB; FIG. 7). Under anaerobic conditions, accumulated reducing equivalents from the fermentative metabolism cannot be oxidized via respiration, as the electron acceptor oxygen is missing. The NAD(P)H reductase protein complex has recently been isolated from plants, and inhibitor experiments have shown evidence of a membrane-bound, chloroplast-located reductase in *C. reinhardtii* (D. Godde et al., *Arch Microbiol.* 127, 245–252 (1980)). The light-dependent electron transport of the H$_2$-evolution is driven by plastoquinone and photosystem I. The donor ferredoxin transfers electrons to the hydrogenase in a final step and molecular hydrogen is released (FIG. 7).

Regulation of hydA at the Transcriptional Level

Studies indicate that there is a correlation between the increase of hydrogen production and the anaerobic adaptation, which was documented by activity measurements (T. Happe et al., *Eur. J. Biochem.* 222, 769–775 (1994)), and immunoblots. It is likely that the induction of hydA is regulated on the level of transcription. It is observed that the amount of mRNA increased directly with the measured H$_2$-evolution. In *C. reinhardtii*, a dramatic change in the hydrogenase transcript level occurs during the shift from an aerobic to an anaerobic atmosphere, which means that the transcription is regulated by the oxygen status of the cells. A very rapid increase of the hyd transcript was detected in the first 30 min of anaerobiosis. This quick increase of gene transcription is only reported for the cyc6 gene in *C. reinhardtii* (K. L. Hill et al., *J. Biol. Chem.* 266, 15060–15067 (1991)) and for the SAUR (Small Auxin-Up RNA) genes in plants (Y. Li et al., *Plant Physiol.* 106, 37–43 (1994)). Interestingly, the hyd, gene of *S. obliquus* is constitutively transcribed under aerobic conditions indicating another regulation system for the expression of the hydrogenase. At the moment, it is not clear if his effect rests upon a new synthesis or a higher stability of the hydA mRNA.

As with other nuclear genes, the promoter region of the hydA from *C. reinhardtii* contains no conserved TATA box or other motif similarities. As no defined motif structures in the promoter region of hydA have been found, further genetic analyses are necessary to investigate the rapid induction of hydA in *C. reinhardtii*.

III. *Chlorella fusca*

The isolation and molecular characterization of the Fe-hydrogenase from the unicellular green alga *Chlorella fusca* was also performed. Hydrogenase activity was observed in a culture of the unicellular green alga *Chlorella fucsa* after anaerobic incubation, but not in the related species *Chlorella vulgaris*. Specific PCR techniques lead to the isolation of the cDNA and the genomic DNA of a special type of [Fe]-hydrogenase in *C. fusca*. The functional Fe-hydrogenase was purified to homogeneity as described above, and its N-terminus was sequenced. The polypeptide sequence shows a high degree of identity with the amino acid sequence deduced from the respective cDNA region. Structural and biochemical analyses indicate that ferredoxin is the main physiological electron donor to this [Fe]-hydrogenase. The nucleotide sequence reported herein has been submitted to the GenBank/EBI Data Bank with accession number AJ 298227. The nucleic acid sequence of the genomic DNA (3,290 bp) of *C. fusca* is set forth in SEQ. ID. NO. 3, and the amino acid sequence of the precursor protein (436 amino acids) is set forth in SEQ. ID. NO. 6. The cDNA sequence is presented in SEQ. ID. NO. 9.

The transcription of the iron-hydrogenase is very rapidly induced during anaerobic adaptation of the green algae. Hydrogen photoproduction by the cells can be observed soon following this induction. The genomic, cDNA and polypeptide sequences of three representative green algae are offered as examples of the properties of the HydA gene and of the enzyme that it encodes. These genomic, cDNA and polypeptide sequences from three representative green algae are also offered as examples of the potential application of the hydA gene from Chlorophyta in the process of commercial hydrogen production:

*Scenedesmus obliquus*

Genomic DNA: 5,001 bp, SEQ. ID NO. 1 (attached hereto)

cDNA: 2,636 bp SEQ. ID NO. 7 (attached)

Precursor protein: 448 amino acids, 44.5 kD, SEQ. ID NO. 4 (attached hereto)

*Chlamydomonas reinhardtii*

Genomic DNA: 5,208 bp, SEQ. ID. NO. 2 (attached)

cDNA: 2,399 bp, SEQ. ID. NO. 8 (attached)

Precursor protein: 497 amino acids, 53.1 kD, SEQ. ID. NO. 5 (attached)

*Chlorella fusca*

Genomic DNA: 3,265 bp, SEQ. ID. NO. 3 (attached)

cDNA: 2,421 bp, SEQ. ID NO. 9 (attached)

Precursor protein: 436 amino acids, SEQ. ID. NO. 6 (attached)

This new class of iron-hydrogenases has a C-terminal portion and active site region (H-cluster) similar to that reported in non-photosynthetic prokaryotes (e.g. *Clostridium pasteurianum*). Cysteine residues and distinct other amino acids which are strictly conserved in the active site (H-cluster) of such non-photosynthetic prokaryotes are also conserved in the iron-hydrogenase of green algae. However, the N-terminal region of the green alga iron-hydrogenase is substantially different from that of HydA in non-photosynthetic prokaryotes, revealing novel and unobvious pathways of electron transport for photosynthetic hydrogen production in green algae.

Distinct iron-sulfur [Fe-S] centers, referred to as FS2, FS4C, FS4B and FS4A, are encountered in the N-terminal region of the iron-hydrogenase in non-photosynthetic prokaryotes, and are thought to be instrumental in the transport of high potential energy electrons from bacterial ferredoxins to the catalytic site of the H-cluster of the hydrogenase. These distinct FS2, FS4C, FS4B and FS4A [Fe-S] centers are missing from the HydA of green algae. A mature-protein folding-model of the green alga iron-hydrogenase and analysis of its structure revealed a protein region of positive surface potential, evidenced by the presence of basic amino acids, which are uniquely localized within the C-terminal domain and, therefore, near the catalytic site of the H-cluster. On the other hand, a model of the structure of green alga ferredoxin, which is different from prokaryotic ferredoxins, revealed negatively charged amino acids near the [2Fe-2S] electron donor site of this molecule. Structural analysis revealed that the [2Fe-2S] center of green algal ferredoxin and the H-cluster of the hydrogenase probably come into close proximity through electrostatic interactions. This molecular geometry is consistent with a direct and efficient electron transfer between these two prosthetic groups. Thus, the hydA gene of green algae encodes an iron-hydrogenase polypeptide with a novel structure, one that uniquely permits a direct coupling and efficient electron-transfer from a [2Fe-2S] photosynthetic ferredoxin to the active site of the H-cluster. In support of this conclusion, inhibitor experiments revealed that the PetF ferredoxin functions as a natural electron donor in green algae, linking the iron-hydrogenase with the photosynthetic electron transport chain in the chloroplast of these unicellular organisms.

In summary, a process, operable in a culture comprising unicellular green algae, is described whereby transcription of algal HydA genomic DNA, followed by translation of the resulting HRNA, followed by targeting of the precursor protein and import of the polypeptide into the chloroplast, followed by the mature iron-hydrogenase folding and catalysis, leads to hydrogen ($H_2$) gas production.

Levels of HydA protein in the cells are very low, even under hydrogen production conditions, and this is a primary reason for the currently low yield of hydrogen production in green algae. It is suggested that genetic engineering of the green algae in order to overexpress the hydA gene would result in strains with far greater yields of hydrogen production, which is of obvious practical importance. Moreover, another use of the hydA genes is that they can be transformed then transferred into other photosynthetic and non-photosynthetic organisms that lack the ability to produce hydrogen. Such genetic transformation with the hydA gene(s) of green algae, will confer to a variety of organisms commercial utility for the production of hydrogen.

There are many species of unicellular green algae that may have variants of the HydA gene described herein for *Scenedesmus obliquus, Chlamydomonas reinhardiii* and *Chlorella fusca*. It is the intended to encompass within the scope of the present invention all green alga HydA genes and gene products that are similar to the unique HydA genes and HydA described herein. A HydA that is "similar" is meant to mean that the HydA has a 75% or greater homology in the amino acid sequence between an isolated HydA and a polypeptide selected from the group consisting of SEQ ID NO. 4, SEQ ID NO. 5, or SEQ ID NO. 6.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

I claim:

1. An isolated nucleic acid sequence comprising SEQ. ID. NO. 2.

2. An isolated nucleic acid sequence comprising SEQ. ID. NO. 8.

3. A cell comprising an isolated nucleic acid sequence encoding a protein comprising SEQ. ID. NO. 5.

* * * * *

SEQUENCE LISTING

<160> NUMBER OF SEQ ID NOS: 9

<210> SEQ ID NO 1
<211> LENGTH: 5001
<212> TYPE: DNA
<213> ORGANISM: Scenedesmus obliquus

<400> SEQUENCE: 1

```
gttgctgttg ctgttctaga acaatccata cacacgatta gattgagctc accttcagct      60
cacggaaaat tcttcaggcc tcaacccttc agctccaccc tgcctttctg gaaaaatgca     120
ctcgtggctc tacagggtga gcaaccaggg gcgcaactgc agggcatgct catacagaac     180
atgctgccgc agctgatcat cgctcagcag tgcagtcaag ctgcgcactg gcagcttgca     240
ttgtagctgg tgtacaacat tccagaagcc gactggtatt cgttgcaatt gtcacaattg     300
tgacgcccat gcaaggccca cgagcaatat cgactgcaga accctgtgct gggatctacg     360
ggaatgattg gattggacga tgtcagggcg ttcgacagca ccgtaccaaa gcttgccaaa     420
ctttagcagc ggctgctagc aaccacgaga taagccatgg ccacaacctt gcaacatcgc     480
gcatctgcag ccgccgatgc atgcaaggtc ggtgttgtgc ggttcctgct tgctctgctt     540
caggcaacac agcctccagg tgttcaactt gaaggtgtga caccactggt gtgctggcag     600
ctggccattc ggtttaagcc aagcagtaca gcgctgtcag cttcatcccc gcctggttac     660
tgtgatgtat gtgcttctga tcaagcggtc ctccatgccg tccgaacaga actgcgctgt     720
aagcttacgc agccccaacc ggctccgagc agcatgccct taagtggcgg gaaaactgcc     780
agggacggtg taagggcgcc attcagcgct cgatactgta agattgtttt agatgaaaca     840
gaaatacacc tccggagctg cgagtagcga ggtgattttg cataagggat ccacactgtt     900
gtgggcgcac gtccaagaaa tgtttacccg tttcgattga cagcaaaaca tcatgatcat     960
caaaggagtg catcgacagt caacgatcac caggtgatta cgtttgtcac tgacaagcgc    1020
cctctacgtg cgccttgggc ctacatatgc cctgctgtgg gagtacccgt gcacaacaga    1080
gcgttagaga tacttcatag ctgcaactag actaccttta ccctaacgaa atcaccctag    1140
```

-continued

```
accgacagtg tcggagtagc tgcgacccaa acgtgatggc gagcggattg cttctcaagc    1200
agcgctcggt atgcctgagt ggcaaccggg aggtcggtat gctgtttctg tccgcccgcc    1260
agtgaacagg cgggctgtgg tggcagcagg tgcgcttctt ctgaagggca gctagggctg    1320
tttcgggcag tgcatgccgg cctatttttgg gttgctcgga gcaataatat gtactatatt    1380
gctctcgtgg agctgtgttg cgccacgtgc ttgccttggc gcctgttgac cccggacccct    1440 ccacgttgct tcttgccgct gcagagcgca ggcgccttgt tgtgcgggca gctggcccaa    1500
cagcagaatg tgattgccca ccagctcccg cgcccaaggc cccgcactgg cagcagacgc    1560
tagatgagct aggtgagctg cgtgacattg aagtctggt gtccgcaact gctctctgtg    1620
catgctgaca tccggaatca agtgccaaga agcagggctc gtgtgggtca tttgtgggca    1680
ggtttgcagc agcttgccgt gttcaagcag cagcatgtgg gctgacacat actgctgccg    1740
tgcttctgct gtcctgcagc caagcctaag gagcagcgca aggtgatgat cgcccagatc    1800
gcaccagcag tgcgcgtggc tattgcagag accatgggac tcaaccctgg ggatgtgaca    1860
gttggccaga tggtgaccgg cctgcgcatg ctgggctttg attatgtgtt tggtgagtta    1920
cacagtgttt agtgctgcag cagtccagag cagcttgtgc tagttgatgt tgatcctttg    1980
ggcctgggat atccagctgg acgtcttaca ctgttttttt agcgtccgga gtgggctagt    2040
caacaacagt gagcgctgta tcatgtggtt tgttcatgcg tgcgtcgcat gcatgtggcc    2100
taaccagctg ctgccagcgt gtgcatgtgc ttggtgctgt tttggtgctt ggctggtgag    2160
cagccgcttt ctgtgtttat gtttggctcc tgttccatgc atgttctttg ttctgctgtg    2220
actcatctac tgctgctgct ggtgcatctg ctgcttgcag acacgctgtt tggtgctgac    2280
ctcaccatca tggaggaggg cacagagcta cggcacaggc ttcaggtcag tggtgatggt    2340
gtactgctgt gttcattatg ccatgaggga cttgggtgtt gccatcaaca gctcacactt    2400
gtagttactg gcggtagctg cagcgacagg tggatgcata tcctgcagca catatcctgc    2460
agcaggcagc agcattcatg catgcatccc tttgctcccc tgtctccttg tgctgacagt    2520
gctgcacact agcgccagcc acaccaggga tgtcgataac aatcagtctg atgtcatcca    2580
cggtgtttta aaacacatct cttgctgctt gctgcttgca ggaccacctg gagcagcacc    2640
ccaacaagga ggagccgctg cccatgttca ccagctgctg ccctggctgg gtggccatgg    2700
tggagaagtc caaccccgag ctcatcccct acctgtcttc ctgcaagtcg ccccagatga    2760
tgctgggcgc agtcatcaag aactactcg ctgccgaggc cggcgccaag cctgaggaca    2820
tctgcaacgt gagcgtgatg ccctgcgtgc gcaagcaggg cgaggctgac cgcgagtggt    2880
tcaacaccac agggctggc ggcgcgaacg tggaccacgt catgacaact gcagagctgg    2940
gcaagatctt tgtggagcgc ggaatcaagc tgaacgacct gcaggagtcg ccctttgaca    3000
accccgtcgg cgagggcagc ggcggcgcg tgctgttcgg caccactgga ggcgtgatgg    3060
aggcggcgct gcgcaccgtg tacgaagtgg tgagtgtcag tgtggcggca gctgtgggtt    3120
gtatcgcagc agcagtttgc gcatttggca gtagtgcagc atgtgctggc atgcgcagag    3180
ttgcgcccac ctgtgttgga tgtgagctgg gtttgcatag aggcgccatc tgcagaagcg    3240
tgcacttctg catactgctg ctgctgatct actgccttgc cttccaccat acccgccacc    3300
cgtaataatc tctcctgctg cactagccct agacagtgcc agacgttgac gctttctgct    3360
gccgtgttgt gcatctccac gcacctctgc tgcaccgcag gtcacacaga agcctttgga    3420
ccgcatcgtc tttgaggacg tgcgcggcct ggagggcatc aaggagtcca cgctgcacct    3480
```

-continued

```
caccccaggc cccaccagcc ccttcaaggc cttttgcaggc gcagacggca ccggcatcac    3540
cctcaacatc gcggtcgcca acggcctcgg caatgccaag aagctcatca agcagctggc    3600
tgcaggcgag agcaagtacg acttcatcga ggtcatggcc tgccccggcg gctgcatcgg    3660
cggcggcggc cagccgcgca gcgcggacaa gcagatcctg cagaagcgcc aggcggccat    3720
gtacgacctg gacgagcgcg cggtgatccg cgcagccac gagaacccgc tgattggcgc    3780
gctgtatgag aagttcctgg gcgagcccaa cggcccacaag gcgcacgagc tgctgcacac    3840
gcactacgtg gccggcggcg tgcccgatga gaagtgaagc ggtggctggt gatgctggct    3900
gcggcgaaga acggtgggc atggtggtgg gtgggttgct gcatggtggt gtcgctcgtg    3960
cagcatggtg ggtttgcggt tgtgatgttg ggcatgctgc acggaggtgt ttgcatggtt    4020
atggatatgg ttcaggtgct gtgctgcgtc gcatgccata agcaccttgt gaccctgtgc    4080
gatgcataaa aatagatatt gccatttggt tccaggctgg tggtggcagt ggctggttaa    4140
caggggagtg tgtgtgtttg tgtgtcttca ttgtcggtgt gttcttgctg catgtattgt    4200
agtgtaatgg gttatgcacg cctgcatgcg cacgcgctcc tcgtgctgcg acagtgcaca    4260
acgcacagcg tgatacagct gcaggacgtt tgcggaaaaa cacttgttac tggtgacggc    4320
tgaagcagcg atgatggaga gaatggattc gctgctatct cacagggcgt ggctgctgca    4380
tcgccatggc atgtccctgt tgcacgcaat tgcctgcgta attttgatag tggcagcact    4440
gaggcagctg caaggccttc tgccagcggc tgtttgtgtc ctatctgtgt ttacaggcag    4500
ctgcatttga aggcaagggg gttggccatc actcactttg atcactcact ttgaagcagg    4560
cttccatcca tgtattggtc aacgcactga agttcttttt ttgtcaccag gcagcagtat    4620
tgtgtgcaca ctacttgcta tggagatgac agcagcatca atctcaagca tgatgaaagc    4680
gtatgttgta tcagtgcccc attttgcaga ctcttaagag ctttaccttc tcaggggttg    4740
cagcaggtgg tggtcagcca gttgagggag tgtgtggctg ttgtcttgcc accatgtgag    4800
tattgaaacc accatcctga gctaagtgtt caggcatctt accctcatac cccgctaccc    4860
tgctactggg agtttcgttt cattgtattg gcagccgttt actaattagt aatgcgctt    4920 gagcgaggca tgtcttgata tgtatgcctt aggagagtgt gagctcaact caattctcat    4980
aagtgtaagc cacacaactg g                                              5001
```

<210> SEQ ID NO 2
<211> LENGTH: 5208
<212> TYPE: DNA
<213> ORGANISM: Chlamydomonus rheinhardtii

<400> SEQUENCE: 2

```
gatgatatgg atcgtcgtct ggtgctcaag ctcatggggtt ttggctggcc gccgacgctg     60
tcccggaagc accagcagca gcaggggcca ggggtcggg tgatgatgtg ggcgcggtgt    120
atggaggtgg caccctgtat gttcatctgg gcgcttaatt gcgttaagcc attcgagccc    180
acttcggagg caagttcgat ttggtggcgt gagatccgcc tcaccccggt tactgcacgt    240
gcaggagtgg tgtgcagcag tagtcggcag ggtgtcccca ggtattgtgg cgtttgtcgc    300
acggtatgcc ggtgcagtgc tcaggtgcgt aaagcggcgc gtcgcggtgt tggtcgcaac    360
cggatgcttg aagccgaaat cgcttcgtcg gcacgtgtaa gtcattgttt gtttgggtga    420
gctttgctgg cagcgtagaa ccgctgtggc ggacacacgc tcagcaaggg ccaagggggg    480
cgtccaagcc aaggtccaag cgcgcatccc ctcaccccctg caccaatgtc caacaccgac    540
agtaatccac gctccgctac gtcgcaagca ggcaatcatg cgtgtctaac atgactgaac    600
```

```
tgccccgctg cccgtgaagg gcgatcgtca cgaagttttg tttgcatggt cgtatcggtg    660
tatatgcgca cgcattgttg ccgacacaac ggacacaact atccggctgc ctactgttgt    720
ataagggtca tagaatctag cgttatcctt ccacgagcgt gtggcagcct gctggcgtgg    780
acgagctgtc atgcgttgtt ccgttatgtg tcgtcaaacg ccttcgagcg ctgcccggaa    840
caatgcgtac tagtatagga gccatgaggc aagtgaacag aagcgggctg actggtcaag    900
gcgcacgata gggctgacga gcgtgctgac ggggtgtacc gccgagtgtc cgctgcattc    960
ccgccggatt gggaaatcgc gatggtcgcg cataggcaag ctcgcaaatg ctgtcagctt   1020
atcttacatg aacacacaaa cactctcgca ggcactagcc tcaaaccctc gaaacctttt   1080
tccaacagtt tacaccccaa ttcggacgcc gctccaagct cgctccgttg ctccttcatc   1140
gcaccaccta ttatttctaa tatcgtagac gcgacaagat gtcggcgctc gtgctgaagc   1200
cctgcgcggc cgtgtctatt cgcggcagct cctgcagggc gcggcaggtc gcccccccgcg   1260 ctccgctcgc agccagcacc gtgcgtgtag cccttgcaac acttgaggcg cccgcacgcc   1320
gcctagggtg agggcgacgc agtgaacgca gtttcgatgg gtcactttgt cgcttttgcg   1380
gaagcctccg aaacgtcccg cgaggttcaa acggccccga atgaccacac ccatatggcc   1440
actgggaata ataacgcagc aacgtcgctt cgcggctgc cgcacccgct gcggaggcgc   1500 cttttgagtca tgtccagcag gcgctcgccg agcttggagc gaacggccga gcgagcgcgc   1560
acgcattgtt gtggtcaagt ctctccactc agtccgaccc cccacacggc gtagggtct    1620 gaagtccacc aactcctcac acaccccaag gaagggacga agcccccct ggctacgctt    1680 tacccagcag ccacagcgac agagcgcccc aacataggct cgagatagaa cgcacctgaa   1740
ctgtgacact tacaatggaa aggaactgcg gatggcctta aagtcaagca ttttgtgacg   1800
agtcggctcg gaatccccat cggcgcccgt ccgttcgtct tcatcaccgc ctgaaacggc   1860
gcacgcgcaa tagtgcgcac ttgatgcctt tcggtccaac gcctctgtca gctaacactt   1920
tccagggcca gcgcggactc gagaaccctc tttcctggca accttggttt ggctggacct   1980
ggcaaccttg gtttgctgg caccaacctt gaccccacata aatctctccc cccccccctt   2040
atgcccacag ccaagcccaa ggacgacccc acgcgcaagc acgtctgcgt gcaggtggct   2100
ccggccgttc gtgtcgctat tgccgagacc ctgggcctgg cgccgggcgc caccacccccc   2160 aagcagctgg ccgagggcct ccgccgcctc ggctttgacg aggtaggtgc gctcgctgct   2220
gcagtgccca acacgcatct tccagctcac cgcctccagt cagcaccttg gcatgcatgc   2280
ttggcgcatc tgccgcctca ttgccgcctc gcggcctcgc cgctgcctgc atcaagcctg   2340
cctgcctgcc tgcccgccct cacgcccag gtgtttgaca cgctgtttgg cgccgacctg   2400
accatcatgg aggagggcag cgagctgctg caccgcctca ccgagcacct ggaggcccac   2460
ccgcactccg acgagccgct gcccatgttc accagctgct gccccggctg gatcggtagc   2520
agcgcggcgt gcttgcttag ggccccataa cctgtcttgg gccccggcg tccgcctctc    2580 cacctacctg caacatgtac gtgcctacgg tattgtcgca tgtctcttga cgatttgggt   2640
cgaccttacc tttgccttgt gtcctttctc caccccacc cgcctctttc ctcgccggcc    2700
cccctcgcgc agctatgctg gagaaatctt acccggacct gatcccctac gtgagcagct   2760
gcaagagccc ccagatgatg ctggcggcca tggtcaagtc ctacctagcg gaaaagaagg   2820
gcatcgcgcc aaaggacatg gtcatggtgt ccatcatgcc ctgcacgcgc aagcagtcgg   2880
aggctgaccg cgactggttc tgtgtggacg ccgaccccac cctgcgccag ctggaccacg   2940
```

```
tcatcaccac cgtggagctg ggcaacatct tcaaggagcg cggcatcaac ctggccgagc    3000
tgcccgaggg cgagtgggac aatccaatgg gcgtgggctc gggcgccggc gtgctgttcg    3060
gcaccaccgg cggtgtcatg gaggcggcgc tgcgcacggt gggtctgtga gagccggttg    3120
attggcccgg cagaacgcat acacttgctg aacctttgat gcgggataag caaggctacc    3180
gatccgcgtc ttttacacc tgtttatcac gtcgctgagc aagctcgtga cacctgcagg    3240
cctatgagct gttcacgggc acgccgctgc cgcgcctgag cctgagcgag gtgcgcggca    3300
tggacggcat caaggagacc aacatcacca tggtgcccgc gcccgggtcc aagtttgagg    3360
agctgctgaa gcaccgcgcc gccgcgcgcg ccgaggccgc cgcgcacggc accccgggc    3420 cgctggcctg ggacggcggc gcgggcttca ccagcgagga cggcaggggc ggcatcacac    3480
tgcgcgtggc cgtggccaac gggctgggca acgccaagaa gctgatcacc aagatgcagg    3540
ccggcgaggc caagtacgac tttgtggaga tcatggcctg ccccgcgggc tgtgtgggcg    3600
gcggcggcca gccccgctcc accgacaagg ccatcacgca gaagcggcag gcggcgctgt    3660
acaacctgga cgagaagtga gcgggcggcg ctgctgggat tgggcagggg agggaaggga    3720
ctgcggggca gggtgcggcg ggaaacggaa atgggcaagg ctcgaggtgg agggcggggt    3780
gggttggggt tacttgctac aggttggcgg gcaggatgtg atggaagcag tgtggaggag    3840
gtgtgcgtag ggtcccgacg acggtattcg cacgagcaaa gagggtcggc acttcctgac    3900
acaatgtgcg cctgcacgtg cgctcctgtt gctgccccag gtccacgctg cgccgcagcc    3960
acgagaaccc gtccatccgc gagctgtacg acacgtacct cggagagccg ctgggccaca    4020
aggtgggggg ggttgtatac taccagccca aatgacgggg ctggtcgggg gcgttggaga    4080
ggcgggccgg gagggaggcg ggctgggtgt ggggcaacag caggtgaagg gacggggggg    4140
cgcactgggc agggcggtac atgccttgtc ctgatagcta cccacacgcg actgttgcta    4200
catggatgca tgacgtgtgc cgtgtgcttg acccctgcag gcgcacgagc tgctgcacac    4260
ccactacgtg gccggcggcg tggaggagaa ggacgagaag aagtgaggag cgccagaggc    4320
tctttgggcg gagacagctt caaagcgagg gggcgtatta gcagtaccgt aaatatgcac    4380
tgatgggtga tgcgggtgtc ctcctttata ttgaatgggg tcaaaatagg cggcgggtca    4440
aatgtttcct ttttgagtgg tgtcacagca tggggcacgt gtgcggaggc cagttgccct    4500
ccagtgcacg cgctcccggt gtgtggccgc actggccttg gataatgcac cggtggagga    4560
ttatggaaga gggggactca gaaggctcat tattggacaa tgcctggtct cttccacatt    4620
ggtgtgagcg cggctccgca taggctgttc actgcacgct ggcattaggc gtaggtactg    4680
gcatgaggga gcgcggcttg ctaaccgaat ggcgtatccc tccagggcac gtcggaatgg    4740
cgcgtgccca tcaacgcaaa ttcttggcct tcatcgcttc tggatattga agctcacaa     4800 acctgcattc tatttgcttg tttacacgtg ccccaatctt ggttggaagc taaacatgtt    4860
tgggaacaat tcatcttact aaagcgtgtg ggggttgagg atgcgcacgt tgtgcgctgg    4920
tgggtgggcg ggaacgtggg tagcatttag gctagctggc atacgacaac ggggcccgtg    4980
aggattgagc acttgactcg cgaacttatg aactagcgc tttataccca ccgtatgcga     5040
ttgacgttgg tgtaggcaac caggcggtag gaaggcggag agatgcattg caaacgcctg    5100
taaaagaacg gcatagctac tagacactct gatgtggacc cttggcgcag ccacgacagg    5160
agaggtgtgc atcagccgct tgtaagcacg cacttctgag aaaaaaaa                 5208
```

<210> SEQ ID NO 3
<211> LENGTH: 3265

<212> TYPE: DNA
<213> ORGANISM: Chlorella fusca

<400> SEQUENCE: 3

| | | | | | |
|---|---|---|---|---|---|
| gcggaattac | tagtgataag | cagtggtaac | aacgcagagt | cgcgggcagg | gactcgatca | 60 |
| gttgttatgt | gttgccccgt | ggttgcaagt | aggcacgcag | ggcgtgcaag | gcatgttgct | 120 |
| gtccgtgcag | cagggccaac | atctgagtgt | gattgtcctc | caacacctca | ggccaagctg | 180 |
| cctcactggc | agcaggctct | ggatgagctc | gccaagccca | aggagagcag | gaggttgatg | 240 |
| atcgcgcaaa | tcgcctccgc | tgttcgtgtc | gctattgctg | agaccattgg | cttggcccca | 300 |
| ggagatgtca | ccattgggca | gctcgtgact | gggctgcgta | tgcttggctt | tgattatgtc | 360 |
| tttggtaagc | agcagcatct | tgcattacac | ttgcagttgg | tcgtcacatg | cacctaatca | 420 |
| gatgttagcc | ctctggaaca | ttttttgcctg | tttggtgctt | acctgaccaa | ctgctgcctg | 480 |
| gtatggccaa | cttgtgaagc | tgcgtgtgtt | ggcgttgcta | cagacaccct | gtttggtgct | 540 |
| gacctgacca | ttatggagga | gggaacggag | ctgctgcatc | gcctgcagga | ccatctggag | 600 |
| cagcacccca | caaggaggt | gagtaagcca | gctgggtggt | ctaccaccca | gcaccagctc | 660 |
| gagacagcag | ccttgcatca | acactcacaa | cgtctagctc | ctccttaaat | gagcggacca | 720 |
| aacctgtgag | tggcaccatg | tcagctgccc | ctcgcaccaa | agcacagcat | ggcctgtctg | 780 |
| tcgtcgattg | ccacatgagt | gtttgcgttg | ttatgcaagt | gcctgaacaa | actgcatatt | 840 |
| cctgtgtctc | tctgcgttcg | cacaggagcc | actgcccatg | ttcaccagtt | gctgcccagg | 900 |
| ctgggttgcc | atggttgaaa | agagcaatcc | tgagctcatc | ccctacctgt | catcttgcaa | 960 |
| gtcgcctcag | atgatgcttg | gggccgttat | caagaactac | tatgcacagc | aggttggagt | 1020 |
| gcagcccagt | gacatctgca | acgtgtcagt | catgccatgc | gtacgcaagc | agggagaggc | 1080 |
| tgaccgggag | tggttcaaca | ccacaggtgg | gcgcaggcag | tgtatcacca | gtactggtgt | 1140 |
| tctccgtgtg | ttgtcagtgt | gtctgttaga | ggctggatac | tctccagtgc | agtgctgatg | 1200 |
| cagagtggcg | gctggtgtgc | agcagcgacc | ccaagaacac | tgagagctgg | caattcaatg | 1260 |
| ggcttgcttg | cttactgtca | gcttcctttt | cctgcaggtg | cagtgacata | cggtctgcat | 1320 |
| caaggctcaa | acatgttgtg | tatgtatgtg | tgatgttgca | attgcaggcc | ttgcccgtga | 1380 |
| tgttgatcat | gtggtgacta | ctgctgaggt | tggtaagata | ttcctggagc | gtggcatcaa | 1440 |
| gctgaatgag | ctgccagaga | gcaactttga | caaccccatt | ggcgagggca | caggtggtgc | 1500 |
| tctgctgttt | ggcaccactg | gaggtgtcat | ggaggcagca | cttcgcacag | tctatgaagt | 1560 |
| ggtgagtggt | actgcttcag | tttcagtcag | tgtaccaacc | aagctactgc | aattgcatag | 1620 |
| cgccagtttt | ctgccatcaa | tgacctgctt | tgtaagtagc | tgatacttta | ccaaccactg | 1680 |
| gtatttgtgg | ttatcctgcc | atagcacatg | ccttctcctg | ctgttggctt | tatcaacctg | 1740 |
| ttggtctatg | tgtcactgct | gtgctgcagg | ttacccagaa | gcccatgggt | cgtgttgact | 1800 |
| tgaggaggt | gcgaggcctt | gaaggaatca | aggaggcaga | gatcacactc | aagccaggag | 1860 |
| acgacagccc | attcaaagcc | ttcgcaggag | ctgatgggca | gggcatcacg | ctcaagattg | 1920 |
| cagtagccaa | tgggcttggc | aatgccaaga | agctcatcaa | gagcctgtca | gagggcaagg | 1980 |
| ccaagtatga | tttcattgag | gtcatggcat | gccctggtgg | ctgcattggc | ggaggcggtc | 2040 |
| agccccgcag | tactgacaag | cagatcctgc | agaagcgcca | gcaggctatg | tacaacctgg | 2100 |
| atgagcgcag | taccatccgc | cgcagccatg | ataacccatt | catccaggcg | ctgtatgaca | 2160 |
| agttcctagg | cgcaccccaac | agccacaagg | cacatgatct | gctgcacaca | cactatgtgg | 2220 |

-continued

```
caggtggaat tccagaggag aagtgaggga ccgaggccgg agtggtgtta ttagtgtaga    2280
gctaggcagc agggatctgg ccgcatttgg gtgctgttgt ttggtttggc atcaaagata    2340
tgatgaatgt acaatctatt gggttctttg tatctcattc atgactgctg cttggtgagg    2400
tatgggccag gaagaagccc gcatcaatgc atgtgaacta ggtggctcca catatgaacc    2460
ctatctggat gtttaaggta cctgaaacaa tagtgcatcg gctctgcatg gctcaacaac    2520
ctgtcttcag agcaggtgta ttccacacca tcttgattta cctaccactc tgtagttcaa    2580
gtggtcaaat tgaatgtcta tggcagctac gcctgcagtt catagtctat gaaggtttca    2640
ccagagtcca tgtccctcat attttttgtt ttatatgcct tgattatgcc ccttgaacca    2700
tgctcaatgc acacaagttg gtcgcaggac aggcggcatc gtacatctca attttcagaa    2760
cttgtcagtg cggcattgcc ttatttgtac tcttgcagtc ctgtttcacc cttgctactg    2820
ccttgcatgc atcttgtttt tgcaagcaac agctcatgca ttgcaatcga tcatcacgta    2880
catccgtgcc atattcacat ggttttgact gcaaatcaa ccaccaggca gtgggtaaat    2940
tgccaggctg ggtgcacttt gggccatttg gcagccctc ttgtggcgag ctttgctgca    3000
gggccaagct gagtgcatca gactcagcag gctgctgctg gcactgtaga atgctgaaaa    3060
gggcattcaa ctacatgtca ttattaggtt gacctgagac agccgtaaga atatcattgt    3120
gtgctgaact tagtcgtcaa tgtcatgcca tgatgtgtgt ttcagggatg gataagggag    3180
gtccttcctc aattacatgc ctttcaagag acttcaatat ctgttgtcag tgacttgttt    3240
gtgtttgctt aatccagtgg ttctc                                          3265
```

<210> SEQ ID NO 4
<211> LENGTH: 448
<212> TYPE: PRT
<213> ORGANISM: Scenedesmus obliquus

<400> SEQUENCE: 4

```
Met Pro Glu Trp Gln Pro Gly Gly Arg Tyr Ala Val Ser Val Arg Pro
 1               5                  10                  15

Pro Val Asn Arg Arg Ala Val Val Ala Ala Glu Arg Arg Arg Leu Val
            20                  25                  30

Val Arg Ala Ala Gly Pro Thr Ala Glu Cys Asp Cys Pro Pro Ala Pro
        35                  40                  45

Ala Pro Lys Ala Pro His Trp Gln Gln Thr Leu Asp Glu Leu Ala Lys
    50                  55                  60

Pro Lys Glu Gln Arg Lys Val Met Ile Ala Gln Ile Ala Pro Ala Val
65                  70                  75                  80

Arg Val Ala Ile Ala Glu Thr Met Gly Leu Asn Pro Gly Asp Val Thr
                85                  90                  95

Val Gly Gln Met Val Thr Gly Leu Arg Met Leu Gly Phe Asp Tyr Val
            100                 105                 110

Phe Asp Thr Leu Phe Gly Ala Asp Leu Thr Ile Met Glu Glu Gly Thr
        115                 120                 125

Glu Leu Leu His Arg Leu Gln Asp His Leu Gln His Pro Asn Lys
    130                 135                 140

Glu Glu Pro Leu Pro Met Phe Thr Ser Cys Cys Pro Gly Trp Val Ala
145                 150                 155                 160

Met Val Glu Lys Ser Asn Pro Glu Leu Ile Pro Tyr Leu Ser Ser Cys
                165                 170                 175

Lys Ser Pro Gln Met Met Leu Gly Ala Val Ile Lys Asn Tyr Phe Ala
            180                 185                 190
```

```
Ala Glu Ala Gly Ala Lys Pro Glu Asp Ile Cys Asn Val Ser Val Met
            195                 200                 205
Pro Cys Val Arg Lys Gln Gly Glu Ala Asp Arg Glu Trp Phe Asn Thr
        210                 215                 220
Thr Gly Ala Gly Gly Ala Asn Val Asp His Val Met Thr Thr Ala Glu
225                 230                 235                 240
Leu Gly Lys Ile Phe Val Glu Arg Gly Ile Lys Leu Asn Asp Leu Gln
                245                 250                 255
Glu Thr Pro Phe Asp Asn Pro Val Gly Glu Gly Ser Gly Gly Val Leu
            260                 265                 270
Phe Gly Thr Thr Gly Gly Val Met Glu Ala Ala Leu Arg Thr Val Tyr
        275                 280                 285
Glu Val Val Thr Gln Lys Pro Leu Asp Arg Ile Val Phe Glu Asp Val
        290                 295                 300
Arg Gly Leu Glu Gly Ile Lys Glu Ser Thr Leu His Leu Thr Pro Gly
305                 310                 315                 320
Pro Thr Ser Pro Phe Lys Ala Phe Ala Gly Ala Asp Gly Thr Gly Ile
                325                 330                 335
Thr Leu Asn Ile Ala Val Ala Asn Gly Leu Gly Asn Ala Lys Lys Leu
            340                 345                 350
Ile Lys Gln Leu Ala Ala Gly Glu Ser Lys Tyr Asp Phe Ile Glu Val
        355                 360                 365
Met Ala Cys Pro Gly Gly Cys Ile Gly Gly Gly Gln Pro Arg Ser
        370                 375                 380
Ala Asp Lys Gln Ile Leu Gln Lys Arg Gln Ala Ala Met Tyr Asp Leu
385                 390                 395                 400
Asp Glu Arg Ala Val Ile Arg Arg Ser His Glu Asn Pro Leu Ile Gly
                405                 410                 415
Ala Leu Tyr Glu Lys Phe Leu Gly Glu Pro Asn Gly His Lys Ala His
            420                 425                 430
Glu Leu Leu His Thr His Tyr Val Ala Gly Gly Val Pro Asp Glu Lys
        435                 440                 445

<210> SEQ ID NO 5
<211> LENGTH: 497
<212> TYPE: PRT
<213> ORGANISM: Chlamydomonas rheinhardtii

<400> SEQUENCE: 5

Met Ser Ala Leu Val Leu Lys Pro Cys Ala Ala Val Ser Ile Arg Gly
1               5                   10                  15
Ser Ser Cys Arg Ala Arg Gln Val Ala Pro Arg Ala Pro Leu Ala Ala
            20                  25                  30
Ser Thr Val Arg Val Ala Leu Ala Thr Leu Glu Ala Pro Ala Arg Arg
        35                  40                  45
Leu Gly Asn Val Ala Cys Ala Ala Ala Pro Ala Ala Glu Ala Pro
    50                  55                  60
Leu Ser His Val Gln Gln Ala Leu Ala Glu Leu Ala Lys Pro Lys Asp
65                  70                  75                  80
Asp Pro Thr Arg Lys His Val Cys Val Gln Val Ala Pro Ala Val Arg
                85                  90                  95
Val Ala Ile Ala Glu Thr Leu Gly Leu Ala Pro Gly Ala Thr Thr Pro
            100                 105                 110
Lys Gln Leu Ala Glu Gly Leu Arg Arg Leu Gly Phe Asp Glu Val Phe
```

```
            115                 120                 125
Asp Thr Leu Phe Gly Ala Asp Leu Thr Ile Met Glu Glu Gly Ser Glu
    130                 135                 140
Leu Leu His Arg Leu Thr Glu His Leu Glu Ala His Pro His Ser Asp
145                 150                 155                 160
Glu Pro Leu Pro Met Phe Thr Ser Cys Cys Pro Gly Trp Ile Ala Met
                165                 170                 175
Leu Glu Lys Ser Tyr Pro Asp Leu Ile Pro Tyr Val Ser Ser Cys Lys
                180                 185                 190
Ser Pro Gln Met Met Leu Ala Ala Met Val Lys Ser Tyr Leu Ala Glu
            195                 200                 205
Lys Lys Gly Ile Ala Pro Lys Asp Met Val Met Val Ser Ile Met Pro
    210                 215                 220
Cys Thr Arg Lys Gln Ser Glu Ala Asp Arg Asp Trp Phe Cys Val Asp
225                 230                 235                 240
Ala Asp Pro Thr Leu Arg Gln Leu Asp His Val Ile Thr Thr Val Glu
                245                 250                 255
Leu Gly Asn Ile Phe Lys Glu Arg Gly Ile Asn Leu Ala Glu Leu Pro
                260                 265                 270
Glu Gly Glu Trp Asp Asn Pro Met Gly Val Gly Ser Gly Ala Gly Val
            275                 280                 285
Leu Phe Gly Thr Thr Gly Gly Val Met Glu Ala Ala Leu Arg Thr Ala
    290                 295                 300
Tyr Glu Leu Phe Thr Gly Thr Pro Leu Pro Arg Leu Ser Leu Ser Glu
305                 310                 315                 320
Val Arg Gly Met Asp Gly Ile Lys Glu Thr Asn Ile Thr Met Val Pro
                325                 330                 335
Ala Pro Gly Ser Lys Phe Glu Glu Leu Leu Lys His Arg Ala Ala Ala
                340                 345                 350
Arg Ala Glu Ala Ala His Gly Thr Pro Gly Pro Leu Ala Trp Asp
            355                 360                 365
Gly Gly Ala Gly Phe Thr Ser Glu Asp Gly Arg Gly Ile Thr Leu
    370                 375                 380
Arg Val Ala Val Ala Asn Gly Leu Gly Asn Ala Lys Lys Leu Ile Thr
385                 390                 395                 400
Lys Met Gln Ala Gly Glu Ala Lys Tyr Asp Phe Val Glu Ile Met Ala
                405                 410                 415
Cys Pro Ala Gly Cys Val Gly Gly Gly Gln Pro Arg Ser Thr Asp
                420                 425                 430
Lys Ala Ile Thr Gln Lys Arg Gln Ala Ala Leu Tyr Asn Leu Asp Glu
            435                 440                 445
Lys Ser Thr Leu Arg Arg Ser His Glu Asn Pro Ser Ile Arg Glu Leu
    450                 455                 460
Tyr Asp Thr Tyr Leu Gly Glu Pro Leu Gly His Lys Ala His Glu Leu
465                 470                 475                 480
Leu His Thr His Tyr Val Ala Gly Gly Val Glu Glu Lys Asp Glu Lys
                485                 490                 495
Lys

<210> SEQ ID NO 6
<211> LENGTH: 436
<212> TYPE: PRT
<213> ORGANISM: Chlorella fusca
```

<400> SEQUENCE: 6

```
Met Cys Cys Pro Val Val Ala Ser Arg His Ala Gly Arg Ala Arg His
1               5                   10                  15

Val Ala Val Arg Ala Ala Gly Pro Thr Ser Glu Cys Asp Cys Pro Pro
            20                  25                  30

Thr Pro Gln Ala Lys Leu Pro His Trp Gln Gln Ala Leu Asp Glu Leu
                35                  40                  45

Ala Lys Pro Lys Glu Ser Arg Arg Leu Met Ile Ala Gln Ile Ala Ser
        50                  55                  60

Ala Val Arg Val Ala Ile Ala Glu Thr Ile Gly Leu Ala Pro Gly Asp
65                  70                  75                  80

Val Thr Ile Gly Gln Leu Val Thr Gly Leu Arg Met Leu Gly Phe Asp
                85                  90                  95

Tyr Val Phe Asp Thr Leu Phe Gly Ala Asp Leu Thr Ile Met Glu Glu
                100                 105                 110

Gly Thr Glu Leu Leu His Arg Leu Gln Asp His Leu Glu Gln His Pro
            115                 120                 125

Asn Lys Glu Glu Pro Leu Pro Met Phe Thr Ser Cys Cys Pro Gly Trp
130                 135                 140

Val Ala Met Val Glu Lys Ser Asn Pro Glu Leu Ile Pro Tyr Leu Ser
145                 150                 155                 160

Ser Cys Lys Ser Pro Gln Met Met Leu Gly Ala Val Ile Lys Asn Tyr
                165                 170                 175

Tyr Ala Gln Gln Val Gly Val Gln Pro Ser Asp Ile Cys Asn Val Ser
            180                 185                 190

Val Met Pro Cys Val Arg Lys Gln Gly Glu Ala Asp Arg Glu Trp Phe
            195                 200                 205

Asn Thr Thr Gly Ala Gly Leu Ala Arg Asp Val Asp His Val Val Thr
            210                 215                 220

Thr Ala Glu Val Gly Lys Ile Phe Leu Glu Arg Gly Ile Lys Leu Asn
225                 230                 235                 240

Glu Leu Pro Glu Ser Asn Phe Asp Asn Pro Ile Gly Glu Gly Thr Gly
                245                 250                 255

Gly Ala Leu Leu Phe Gly Thr Thr Gly Gly Val Met Glu Ala Ala Leu
                260                 265                 270

Arg Thr Val Tyr Glu Val Val Thr Gln Lys Pro Met Gly Arg Val Asp
            275                 280                 285

Phe Glu Glu Val Arg Gly Leu Glu Gly Ile Lys Glu Ala Glu Ile Thr
            290                 295                 300

Leu Lys Pro Gly Asp Asp Ser Pro Phe Lys Ala Phe Ala Gly Ala Asp
305                 310                 315                 320

Gly Gln Gly Ile Thr Leu Lys Ile Ala Val Ala Asn Gly Leu Gly Asn
                325                 330                 335

Ala Lys Lys Leu Ile Lys Ser Leu Ser Glu Gly Lys Ala Lys Tyr Asp
            340                 345                 350

Phe Ile Glu Val Met Ala Cys Pro Gly Gly Cys Ile Gly Gly Gly Gly
            355                 360                 365

Gln Pro Arg Ser Thr Asp Lys Gln Ile Leu Gln Lys Arg Gln Gln Ala
        370                 375                 380

Met Tyr Asn Leu Asp Glu Arg Ser Thr Ile Arg Arg Ser His Asp Asn
385                 390                 395                 400

Pro Phe Ile Gln Ala Leu Tyr Asp Lys Phe Leu Gly Ala Pro Asn Ser
                405                 410                 415
```

His Lys Ala His Asp Leu Leu His Thr His Tyr Val Ala Gly Gly Ile
            420                 425                 430

Pro Glu Glu Lys
      435

<210> SEQ ID NO 7
<211> LENGTH: 2636
<212> TYPE: RNA
<213> ORGANISM: Scenedesmus obliquus

<400> SEQUENCE: 7

| | | | | |
|---|---|---|---|---|
| acaacagagc | guuagagaua | cuucauagcu | gcaacuagac | uaccuuuacc cuaacgaaau | 60 |
| cacccuagac | cgacaguguc | ggaguagcug | cgacccaaac | gugauggcga gcggauugcu | 120 |
| ucucaagcag | cgcucgguau | gccugagugg | caaccgggag | gucgguaugc uguuucuguc | 180 |
| cgcccgccag | ugaacaggcg | ggcugugugu | gcagcagagc | gcaggcgccu uguugugcgg | 240 |
| gcagcuggcc | caacagcaga | augugauugc | ccaccagcuc | ccgcgcccaa ggccccgcac | 300 |
| uggcagcaga | cgcuagauga | gcuagccaag | ccuaaggagc | agcgcaaggu gaugaucgcc | 360 |
| cagaucgcac | cagcagugcg | cguggcuauu | gcagagacca | ugggacucaa cccuggggau | 420 |
| gugacaguug | gccagauggu | gaccggccug | cgcaugcugg | gcuuugauua uguguuugac | 480 |
| acgcuguuug | gugcugaccu | caccaucaug | gaggagggca | cagagcuacu gcacaggcuu | 540 |
| caggaccacc | uggagcagca | ccccaacaag | gaggagccgc | ugcccauguu caccagcugc | 600 |
| ugcccuggcu | ggguggccau | gguggagaag | uccaacccccg | agcucauccc cuaccugucu | 660 |
| uccugcaagu | cgccccagau | gaugcugggc | gcagucauca | agaacuacuu cgcugccgag | 720 |
| gccggcgcca | agccugagga | caucugcaac | gugagcguga | ugcccugcgu gcgcaagcag | 780 |
| ggcgaggcug | accgcgagug | guucaacacc | acaggggcug | gcggcgcgaa cguggaccac | 840 |
| gucaugacaa | cugcagagcu | gggcaagauc | uuuguggagc | gcggaaucaa gcugaacgac | 900 |
| cugcaggaga | cgcccuuuga | caaccccguc | ggcgagggca | gcggcggcgu acuguucggc | 960 |
| accacuggag | gcgugaugga | ggcggcgcug | cgcaccgugu | acgaaguggu cacacagaag | 1020 |
| ccuuuggacc | gcaucgucuu | ugaggacgug | cgcggccugg | agggcaucaa ggaguccacg | 1080 |
| cugcaccuca | ccccaggccc | caccagcccc | uucaaggccu | uugcaggcgc agacggcacc | 1140 |
| ggcaucaccc | ucaacaucgc | ggucgccaac | ggccucggca | ugccaagaa gcucaucaag | 1200 |
| cagcuggcug | caggcgagag | caaguacgac | uucaucgagg | ucauggccug ccccggcggc | 1260 |
| ugcaucggcg | gcggcggcca | ccgcgcagc | gcggacaagc | agauccugca gaagcgccag | 1320 |
| gcggccaugu | acgaccugga | cgagcgcgcg | gugauccggc | gcagccacga gaacccgcug | 1380 |
| auuggcgcgc | uguaugagaa | guuccuggc | gagcccaacg | ccacaaggc gcacgagcug | 1440 |
| cugcacacgc | acuacguggc | cggcggcug | cccgaugaga | gugaagcgg uggcuggugu | 1500 |
| gcuggcugc | ggcgaagaaa | cgguggcau | ggugguggu | ggguugcugc auggugugu | 1560 |
| cgcucgugca | gcaugguggg | uuugcgguug | ugauguugg | caugcugcac ggagguguuu | 1620 |
| gcaugguuau | ggauaugguu | caggugcugu | gcugcgucgc | augccauaag caccuuguga | 1680 |
| cccugugcga | ugcauaaaaa | uagauauugc | cauuugguuc | caggcugugug guggcagugg | 1740 |
| cugguuaaca | ggggagugug | uguguuugug | ugucuucauu | gucgguguug ucuugcugca | 1800 |
| uguauuguag | uguaaugggu | uaugcacgcc | ugcaugcgca | cgcgcuccuc ugcugcgac | 1860 |
| agugcacaac | gcacagcgug | auacagcugc | aggacguuug | cggaaaaaca cuuguuacug | 1920 | gugacggcug aagcagcgau gauggagaga auggauucgc ugcuaucuca cagggcgugg 1980 cugcugcauc gccauggcau gucccuguug cacgcaauug ccugcguaau uuugauagug 2040 gcagcacuga ggcagcugca aggccuucug ccagcggcug uuugugucca aucuguguuu 2100 acaggcagcu gcauuugaag gcaaggggu uggccaucac ucacuuugau cacucacuuu 2160 gaagcaggcu uccauccaug uauuggucaa cgcacugaag uucuuuuuuu gucaccaggc 2220 agcaguauug ugugcacacu acuugcuaug gagaugacag cagcaucaau ucaagcaug 2280 augaaagcgu auguuguauc agugcccau uuugcagacu cuuaagagcu uuaccuucuc 2340 aggguugca gcagguggug ucagccagu ugagggagug uguggcuguu gucuugccac 2400 caugugagua uugaaaccac cauccugagc uaaguguuca ggcaucuuac ccucauaccc 2460 cgcuacccug cuacuggag uuucguuuca uguauuggc agccguuuac uaauuaguaa 2520 uggcgcuuga gcgaggcaug ucuugauaug uaugccuuag gagagugug gcucaacuca 2580 auucucauaa guguaagcca cacaacugga aaaaaaaaaa aaaaaaaaaa aaaaaa 2636

<210> SEQ ID NO 8
<211> LENGTH: 2399
<212> TYPE: RNA
<213> ORGANISM: Chlamydomonas rheinhardtii

<400> SEQUENCE: 8
aucuuacaug aacacacaaa cacucucgca ggcacuagcc ucaaaccccuc gaaaccuuuu 60 uccaacaguu uacaccccaa uucggacgcc gcuccaagcu cgcuccguug cuccuucauc 120
gcaccaccua uuauuucuaa uaucguagac gcgacaagau gucggcgcuc gugcugaagc 180
ccugcgcggc cgugucuauu cgcggcagcu ccugcagggc gcggcagguc gccccccgcg 240
cuccgcucgc agccagcacc gugcguguag cccuugcaac acugaggcg cccgcacgcc 300 gccuaggcaa cgucguuugc gcggcugccg caccgcugc ggaggcgccu uugagucaug 360
uccagcaggc gcucgccgag cuugccaagc ccaaggacga ccccacgcgc aagcacgucu 420
gcgugcaggu ggcuccggcc guucgugucg cuauugccga acccugggc cuggcgccgg 480 gcgccaccac ccccaagcag cuggccgagg gccuccgccg ccucggcuuu gacgaggugu 540
uugacacgcu guuuggcgcc gaccugacca ucauggagga gggcagcgag cugcugcacc 600
gccucaccga gcaccuggag gccccaccgc acuccgacga gccgcugccc auguucacca 660
gcugcugccc cggcuggauc gcuaugcugg agaaaucuua cccggaccug auccccuacg 720
ugagcagcug caagagcccc cagaugaugc uggcggccau ggucaaaguc uaccuagcgg 780
aaaagaaggg caucgcgcca aaggacaugg ucaugugucc caucaugccc ugcacgcgca 840
agcagucgga ggcugaccgc gacugguucu gugggacgc cgaccccacc cugcgccagc 900
uggaccacgu caucaccacc guggagcugg gcaacaucuu caaggagcgc ggcaucaacc 960
uggccgagcu gcccgagggc gagugggaca uccaauggg cgugggcucg ggcgccggcg 1020
ugcuguucgg caccaccggc ggugucaugg aggcggcgcu gcgcacggcc uaugagcugu 1080
ucacgggcac gccgcugccg cgccugagcc ugagcgaggu gcgcggcaug gacggcauca 1140
aggagaccaa caucaccaug gugcccgcgc ccggguccaa guuugaggag cugcugaagc 1200
accgcgccgc cgcgcgcgcc gaggccgccg cgcacgcac ccccgggccg cuggccuggg 1260
acggcggcgc gggcuucacc agcgaggacg cagggggcgg caucacacug cgcguggccg 1320 uggcaacgg gcugggcaac gccaagaagc ugaucaccaa gaugcaggcc ggcgaggcca 1380
aguacgacuu uguggagauc auggccugcc ccgcggggcug gugggcggc ggcggccagc 1440

-continued

```
cccgcuccac cgacaaggcc aucacgcaga agcggcaggc ggcgcuguac aaccuggacg      1500
agaaguccac gcugcgccgc agccacgaga acccguccau ccgcgagcug uacgacacgu      1560
accucggaga gccgcugggc cacaaggcgc acgagcugcu gcacacccac uacguggccg      1620
gcggcgugga ggagaaggac gagaagaagu gaggagcgcc agaggcucuu ugggcggaga      1680
cagcuucaaa gcgaggggc guauuagcag uaccguaaau augcacugau gggugaugcg       1740
ggugucccuc uuuauauuga auggggucaa auaggcggc gggucaaaug uuuccuuuuu       1800
gaguggmguc acagcauggg gcacgugugc ggaggccagu aggcuguuca cugcacgcug      1860
gcauuaggcg uaguacugg caugagggag cgcggcuugc uaaccgaaug gcguaucccu       1920
ccagggcacg ucggaauggc gcgugcccau caacgcaaau ucuuggccuu caucgcuucu      1980
ggauauugaa gcugcacaaa ccugcauucu auuugcuugu uuacacgugc cccaaucuug      2040
guuggaagcu aaacauguuu gggaacaauu caucuuacua aagcgugugg ggguugagga      2100
ugcgcacguu gugcgcuggu ggguggggcg gaacgugggu agcauuuagg cuagcuggca      2160
uacgacaacg gggcccguga ggauugagca cuugacucgc gaacuuauga acguagcgcu      2220
uuauacccac cguaugcgau ugacguuggu uaggcaacc aggcgguagg aaggcggaga       2280
gaugcauugc aaacgccugu aaaagaacgg cauagcuacu agacacucug auguggaccc      2340
uuggcgcagc cacgacagga gaggugugca ucagccgcuu uaagcacgc acuucugag        2399
```

<210> SEQ ID NO 9
<211> LENGTH: 2421
<212> TYPE: RNA
<213> ORGANISM: Chlorella fusca

<400> SEQUENCE: 9

```
gcggaauuac uagugauaag caguggnuaac aacgcagagu cgcgggcagg gacucgauca       60
guuguuaugu guugccccgu gguugcaagu aggcacgcag ggcgugcaag gcauguugcu      120
guccgugcag cagggccaac aucgagugu gauuguccuc caacaccuca ggccaagcug        180
ccucacuggc agcaggcucu ggaugagcuc gccaagccca aggagagcag gagguugaug      240
aucgcgcaaa ucgccuccgc guuucguguc gcuauugcug agaccauugg cuugccccca      300
ggagauguca ccauugggca gcucgugacu gggcugcgua ugcuuggcuu ugauuaugug      360
uuugacaccc uguuuggugc ugaccugacc auuauggagg agggaacgga gcugcugcau      420
cgccugcagg accaucugga gcagcacccc aacaaggagg agccacugcc cauguucacc      480
aguugcugcc caggcugggu ugccauggu gaaaagagca auccgagcu caucccucac       540 cugucaucuu gcaagucgcc ucagaugaug cuuggggccg uuaucaagaa cuacauagca      600
cagcagguug gagugcagcc cagugacauc ugcaacgugu cagucaugcc augcguacgc      660
aagcagggag aggcugaccg ggaguggunc aacaccacag gucaggccu ugcccgugau       720 guugaucaug uggugacuac ugcugaggu gguaagauau uccuggagcg uggcaucaag      780
cugaaugagc ugccagagag caacuuugac aaccccauug gcgagggcac agguggugcu       840
cugcuguuug gcaccacugg aggugucaug gaggcagcac uucgcacagu cuaugaagug      900
gugacccaga agccauggg ucguguugac uuugaggagg ugcgaggccu ugaaggaauc       960
aaggaggcag agaucacacu caagccagga gacgacagcc cauucaaagc cuucgcagga      1020 gcugauggc agggcaucac gcucaagauu gcaguagcca augggcugg caaugccaag      1080 aagcucauca agagccuguc agagggcaag gccaaguaug auuucauuga ggucaauggca     1140
```

-continued

```
ugcccugguq gcugcauugg cggaggcggu cagccccgca guacugacaa gcagauccug    1200
cagaagcgcc agcaggcuau guacaaccug gaugagcgca guaccauccg ccgcagccau    1260
gauaacccau ucauccaggc gcuguaugac aaguuccuag gcgcacccaa cagccacaag    1320
gcacaugauc ugcugcacac acacuaugug gcagguggaa uuccagagga gaagugaggg    1380
accgaggccg gaguggyguu auuaguguag agcuaggcag cagggaucug gccgcauuug    1440
ggugcuguug uuugguuugg caucaaagau augaugaaug uacaaucuau uggguucuuu    1500
guaucucauu caugacugcu gcuuggugag guaugggcca ggaagaagcc cgcaucaaug    1560
caugugaacu agguggcucc acauaugaac ccuaucugga uguuuaaggu accgaaaca     1620 auagugcauc ggcucugcau ggcucaacaa ccugucuuca gagcaggugu auuccacacc    1680
aucuugauuu accaccacu cuguaguuca aguggucaaa uugaaugcu auggcagcua     1740 cgccugcagu ucauagucua ugaagguuuc accagaqucc augcccuca uauuuuugu     1800 uuuauaugcc uugauuaugc cccuugaacc augcucaaug cacacaaguu ggucgcagga   1860
caggcggcau cguacaucuc aauuuucaga acuugucagu gcggcauugc cuuauuugua   1920
cucuugcagu ccuguuucac ccuugcuacu gccuugcaug caucuuguuu uugcaagcaa   1980
cagcucaugc auugcaaucg aucaucacgu acaccguqc cauauucaca ugguuuugac    2040
uugcaaauca accaccaggc aguggguaaa uugccaggcu ggguqcacuu ugggccauuu   2100 gggcagcccu cuuquggcga gcuuugcugc agggccaagc ugaqugcauc agacucagca   2160 ggcugcugcu ggcacuguag aaugcugaaa aqggcauuca acuacauguc auuauuaggu   2220 ugaccuqaga cagccguaag aauaucauug uqugcugaac uuagucguca augucaugcc   2280
augaugugug uuucagggau ggauaaggga gguccuuccu caauuacaug ccuuucaaga   2340
gacuucaaua ucuguugyca gugacuuguu uguguuugcu uaauccagug guucucaaaa   2400
aaaaaaaaaa aaaaaaaaaa a                                             2421
```